United States Patent
McLean et al.

(10) Patent No.: US 10,456,176 B2
(45) Date of Patent: Oct. 29, 2019

(54) APPARATUS AND DEVICES FOR PERCUTANEOUSLY EXTENDING AN EXISTING SPINAL CONSTRUCT

(71) Applicant: SPINE WAVE, INC., Shelton, CT (US)

(72) Inventors: Scott McLean, Sandy Hook, CT (US); Tim E. Adamson, Charlotte, NC (US)

(73) Assignee: SPINE WAVE, INC., Shelton, CT (US)

( * ) Notice: Subject to any disclaimer, the term of this patent is extended or adjusted under 35 U.S.C. 154(b) by 667 days.

(21) Appl. No.: 14/829,040

(22) Filed: Aug. 18, 2015

(65) Prior Publication Data

US 2015/0351811 A1 Dec. 10, 2015

Related U.S. Application Data

(63) Continuation of application No. 14/186,550, filed on Feb. 21, 2014, now Pat. No. 9,113,962, which is a
(Continued)

(51) Int. Cl.
*A61B 17/70* (2006.01)
*A61B 17/88* (2006.01)
(Continued)

(52) U.S. Cl.
CPC ...... *A61B 17/7085* (2013.01); *A61B 17/0218* (2013.01); *A61B 17/3423* (2013.01); *A61B 17/705* (2013.01); *A61B 17/708* (2013.01); *A61B 17/7011* (2013.01); *A61B 17/7032* (2013.01); *A61B 17/7037* (2013.01); *A61B 17/7043* (2013.01); *A61B 17/7049* (2013.01); *A61B 17/7052* (2013.01); *A61B 17/7055* (2013.01); *A61B 17/7091* (2013.01); *A61B 17/88* (2013.01)

(58) Field of Classification Search
CPC .............. A61B 17/7049; A61B 17/705; A61B 17/7052; A61B 17/6466–6483
See application file for complete search history.

(56) References Cited

U.S. PATENT DOCUMENTS

| | | |
|---|---|---|
| 4,611,582 A | 9/1986 | Duff |
| 5,306,275 A | 4/1994 | Bryan |

(Continued)

FOREIGN PATENT DOCUMENTS

| | | |
|---|---|---|
| DE | 9402695 | 5/1994 |
| EP | 0811357 A1 | 12/1997 |

OTHER PUBLICATIONS

Johnson & Johnson Company; DePuy Spine™, Surgical Technique Guide, VIPER™, 3D MIS Correction Set (2011).

*Primary Examiner* — Jacqueline T Johanas
(74) *Attorney, Agent, or Firm* — Hoffmann & Baron, LLP

(57) ABSTRACT

Apparatus and devices for adding an additional spinal construct in a patient are disclosed. In one arrangement the additional spinal construct extends an existing spinal construct ipsilaterally with an inline rod connector in a minimally invasive or preferably, percutaneous procedure. In another arrangement, the ipsilateral extension of an existing spinal construct uses an offset rod connector for receiving an additional spinal rod that may be placed interiorly or exteriorly of the existing spinal construct.

19 Claims, 25 Drawing Sheets

Related U.S. Application Data continuation of application No. 13/470,390, filed on May 14, 2012, now Pat. No. 8,657,826.

(60) Provisional application No. 61/568,199, filed on Dec. 8, 2011.

(51) Int. Cl.
*A61B 17/02* (2006.01)
*A61B 17/34* (2006.01)

(56) References Cited

U.S. PATENT DOCUMENTS

| | | | |
|---|---|---|---|
| 5,330,473 A | 7/1994 | Howland | |
| 5,334,203 A | 8/1994 | Wagner | |
| 5,487,742 A | 1/1996 | Cotrel | |
| 5,520,688 A | 5/1996 | Lin | |
| 5,542,946 A | 8/1996 | Logroscino et al. | |
| 5,569,246 A | 10/1996 | Ojima et al. | |
| 5,630,816 A | 5/1997 | Kambin | |
| 5,688,273 A | 11/1997 | Errico et al. | |
| 5,752,957 A | 5/1998 | Ralph et al. | |
| 5,976,133 A * | 11/1999 | Kraus | A61B 17/171 606/54 |
| 5,984,923 A | 11/1999 | Breard | |
| 6,015,409 A | 1/2000 | Jackson | |
| 6,187,005 B1 | 2/2001 | Brace et al. | |
| 6,273,914 B1 | 8/2001 | Papas | |
| 6,352,537 B1 | 3/2002 | Strnad | |
| 6,368,320 B1 * | 4/2002 | Le Couedic | A61B 17/7049 606/246 |
| 6,379,354 B1 | 4/2002 | Rogozinski | |
| 6,488,682 B2 | 12/2002 | Kikuchi et al. | |
| 6,530,929 B1 | 3/2003 | Justis et al. | |
| 6,626,904 B1 | 9/2003 | Jammet et al. | |
| 6,716,213 B2 | 4/2004 | Shitoto | |
| 6,783,526 B1 | 8/2004 | Lin et al. | |
| 6,802,844 B2 | 10/2004 | Ferree | |
| 7,207,992 B2 | 4/2007 | Ritland | |
| 7,250,052 B2 | 7/2007 | Landry et al. | |
| 7,306,603 B2 | 12/2007 | Boehm, Jr. et al. | |
| 7,465,306 B2 | 12/2008 | Pond, Jr. et al. | |
| 7,476,240 B2 | 1/2009 | Raymond et al. | |
| 7,527,638 B2 | 5/2009 | Anderson et al. | |
| 7,572,276 B2 | 8/2009 | Lim et al. | |
| 7,588,588 B2 | 9/2009 | Spitler et al. | |
| 7,618,442 B2 | 11/2009 | Spitler et al. | |
| 7,648,521 B2 | 1/2010 | Hestad | |
| 7,695,499 B2 | 4/2010 | Morrison et al. | |
| 7,708,763 B2 | 5/2010 | Selover et al. | |
| 7,736,370 B2 | 6/2010 | Sweeney | |
| 7,799,036 B2 | 9/2010 | Davison et al. | |
| 7,824,410 B2 | 11/2010 | Simonson et al. | |
| 7,833,248 B2 * | 11/2010 | Markworth | A61B 17/7049 403/64 |
| 7,905,907 B2 | 3/2011 | Spitler et al. | |
| 7,922,746 B2 | 4/2011 | Miller | |
| 7,931,673 B2 | 4/2011 | Hestad et al. | |
| 8,012,184 B2 | 9/2011 | Schlapfer et al. | |
| 8,021,399 B2 | 9/2011 | Ritland | |
| 8,038,699 B2 | 10/2011 | Cohen et al. | |
| 8,043,343 B2 | 10/2011 | Miller et al. | |
| 8,105,361 B2 | 1/2012 | Anderson et al. | |
| 8,523,906 B2 * | 9/2013 | McLean | A61B 17/7011 606/246 |
| 8,657,826 B2 * | 2/2014 | McLean | A61B 17/7011 606/250 |
| 8,663,281 B2 * | 3/2014 | McLean | A61B 17/7011 606/246 |
| 9,113,962 B2 * | 8/2015 | McLean | A61B 17/7011 |
| 9,138,260 B2 * | 9/2015 | Miller | A61B 17/6466 |
| 9,149,302 B2 * | 10/2015 | McLean | A61B 17/7011 |
| 9,629,668 B2 * | 4/2017 | McLean | A61B 17/7011 |
| 10,206,719 B2 * | 2/2019 | Goel | A61B 17/7032 |
| 2003/0083659 A1 * | 5/2003 | Lin | A61B 17/7052 606/250 |
| 2003/0093078 A1 | 5/2003 | Ritland | |
| 2003/0130659 A1 | 7/2003 | Haider | |
| 2003/0149429 A1 * | 8/2003 | Ferrante | A61B 17/645 606/59 |
| 2003/0208203 A1 | 11/2003 | Lim et al. | |
| 2004/0214326 A1 | 7/2004 | Landry et al. | |
| 2005/0080417 A1 | 4/2005 | Alexis et al. | |
| 2005/0107789 A1 | 5/2005 | Sweeney | |
| 2006/0142758 A1 | 6/2006 | Petit | |
| 2006/0276794 A1 | 12/2006 | Stern | |
| 2007/0016189 A1 | 1/2007 | Lake et al. | |
| 2007/0043357 A1 | 2/2007 | Kirschman | |
| 2007/0043365 A1 | 2/2007 | Ritland | |
| 2007/0088359 A1 | 4/2007 | Woods et al. | |
| 2007/0093827 A1 | 4/2007 | Warnick | |
| 2007/0123862 A1 | 5/2007 | Warnick | |
| 2007/0198014 A1 | 8/2007 | Graf et al. | |
| 2007/0233091 A1 | 10/2007 | Naifeh et al. | |
| 2007/0250061 A1 | 10/2007 | Chin et al. | |
| 2008/0071277 A1 | 3/2008 | Warnick | |
| 2008/0183215 A1 | 7/2008 | Altarac et al. | |
| 2008/0312703 A1 | 12/2008 | Hestad et al. | |
| 2009/0036929 A1 | 2/2009 | Reglos et al. | |
| 2009/0099604 A1 | 4/2009 | Cho et al. | |
| 2009/0099605 A1 | 4/2009 | Fallin et al. | |
| 2009/0177232 A1 | 7/2009 | Kiester | |
| 2009/0187217 A1 | 7/2009 | Weiman et al. | |
| 2009/0210007 A1 | 8/2009 | Levy et al. | |
| 2009/0228046 A1 * | 9/2009 | Garamszegi | A61B 17/7052 606/278 |
| 2010/0049252 A1 | 2/2010 | Smisson, III et al. | |
| 2010/0204733 A1 * | 8/2010 | Rathbun | A61B 17/88 606/251 |
| 2010/0222822 A1 * | 9/2010 | Farris | A61B 17/7004 606/264 |
| 2010/0256683 A1 | 10/2010 | Iott et al. | |
| 2010/0292736 A1 | 11/2010 | Schwab | |
| 2010/0298884 A1 | 11/2010 | Faizan et al. | |
| 2010/0324599 A1 | 12/2010 | Montello et al. | |
| 2011/0087287 A1 | 4/2011 | Reeder, Jr. et al. | |
| 2011/0087288 A1 | 4/2011 | Stevenson et al. | |
| 2011/0098707 A1 * | 4/2011 | Mullaney | A61B 17/6466 606/59 |
| 2011/0106085 A1 | 5/2011 | Null et al. | |
| 2011/0106164 A1 | 5/2011 | Wilcox et al. | |
| 2011/0106166 A1 | 5/2011 | Keyer et al. | |
| 2011/0172717 A1 * | 7/2011 | Miller | A61B 17/7014 606/279 |
| 2011/0208245 A1 * | 8/2011 | Broman | A61B 17/7011 606/278 |
| 2011/0313323 A1 | 12/2011 | Henderson | |
| 2011/0313460 A1 | 12/2011 | McLean et al. | |
| 2012/0004659 A1 * | 1/2012 | Miller | A61B 17/60 606/54 |
| 2012/0010664 A1 | 1/2012 | Ritland | |
| 2012/0095462 A1 * | 4/2012 | Miller | A61B 17/6466 606/59 |

* cited by examiner

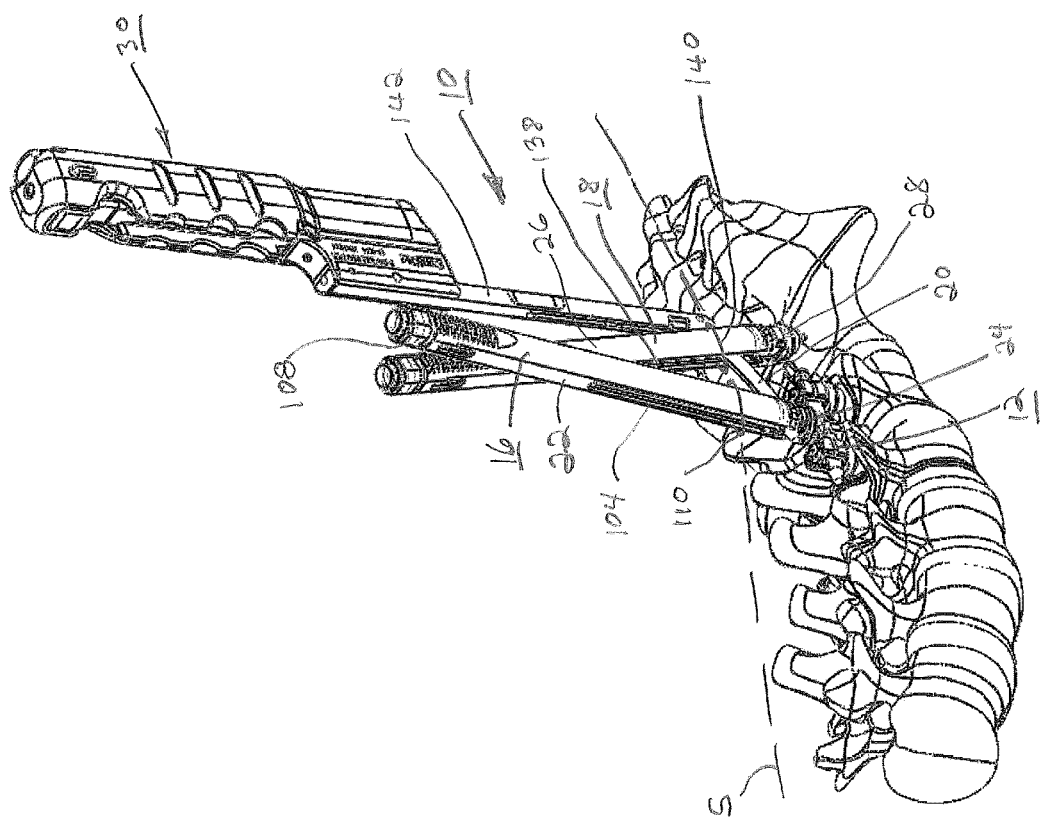

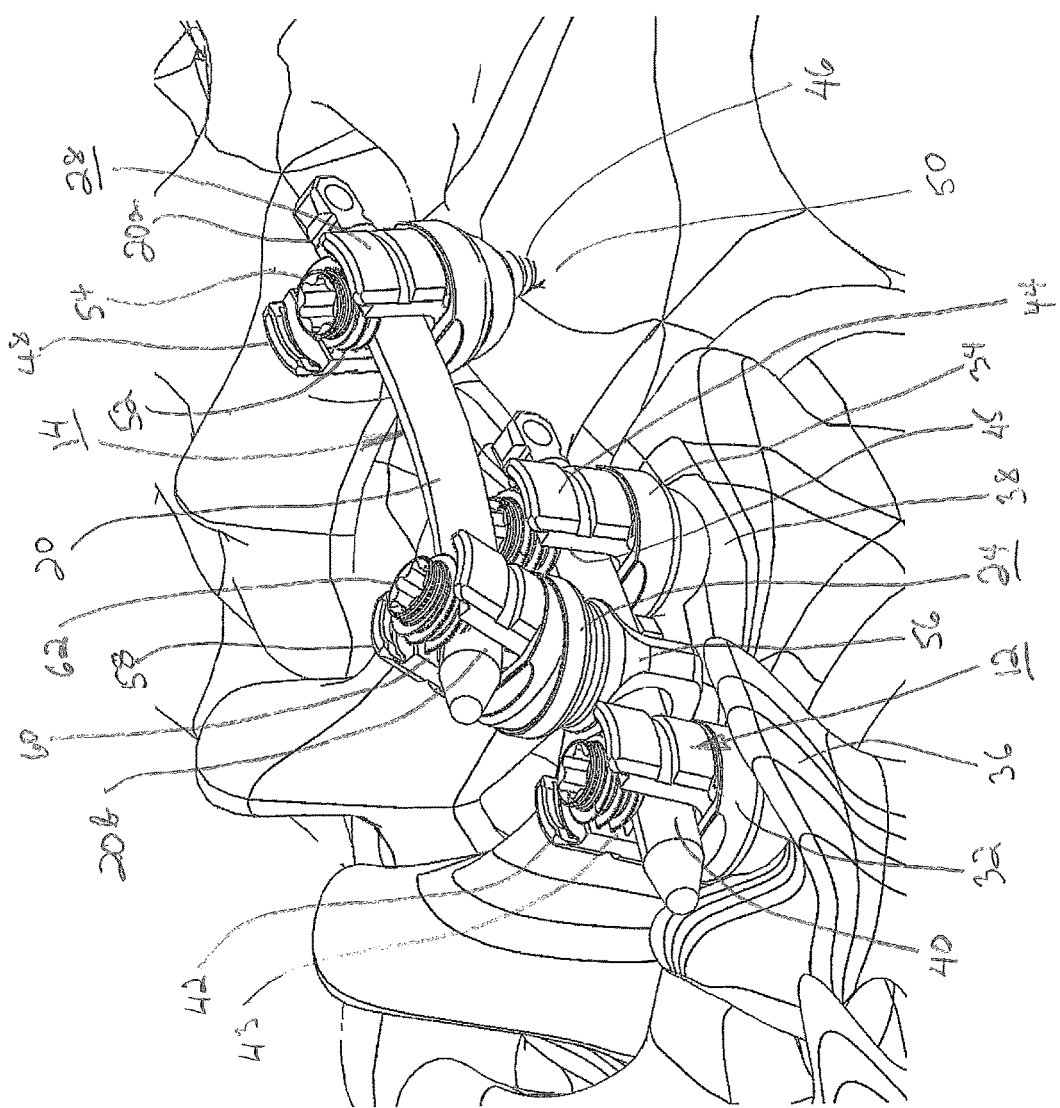

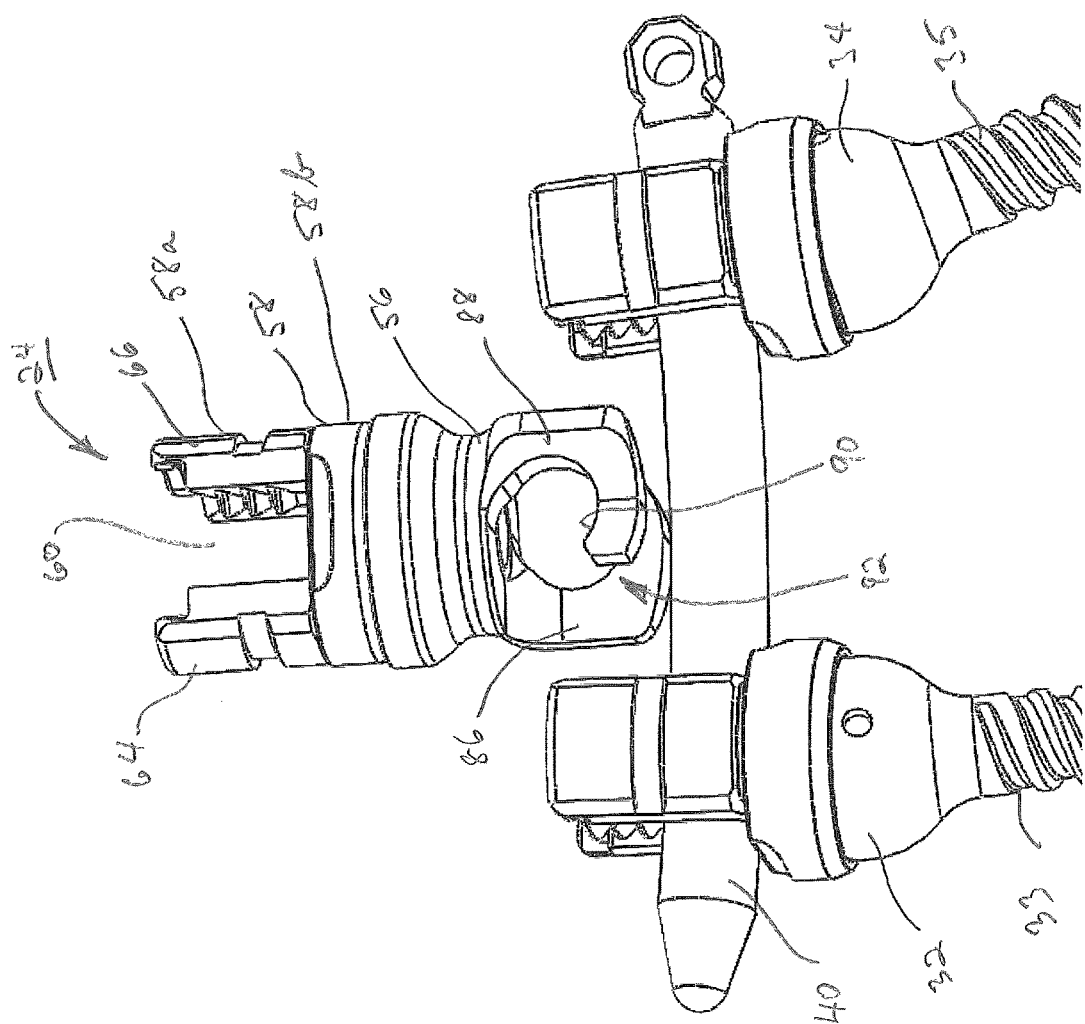

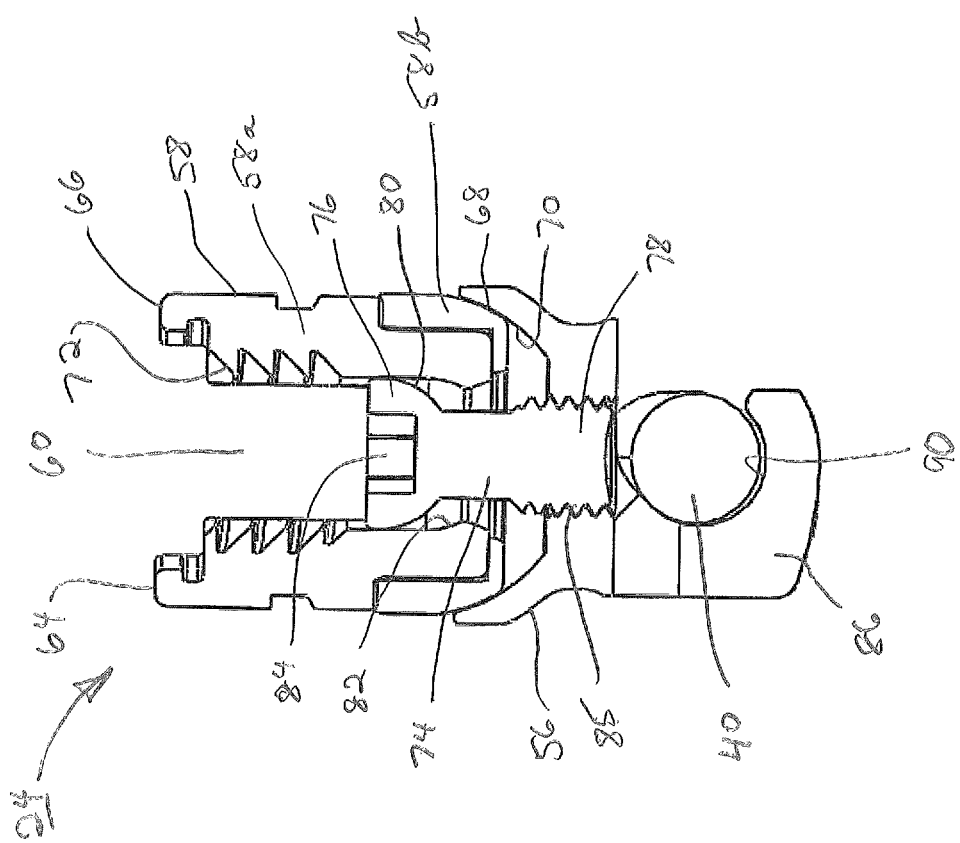

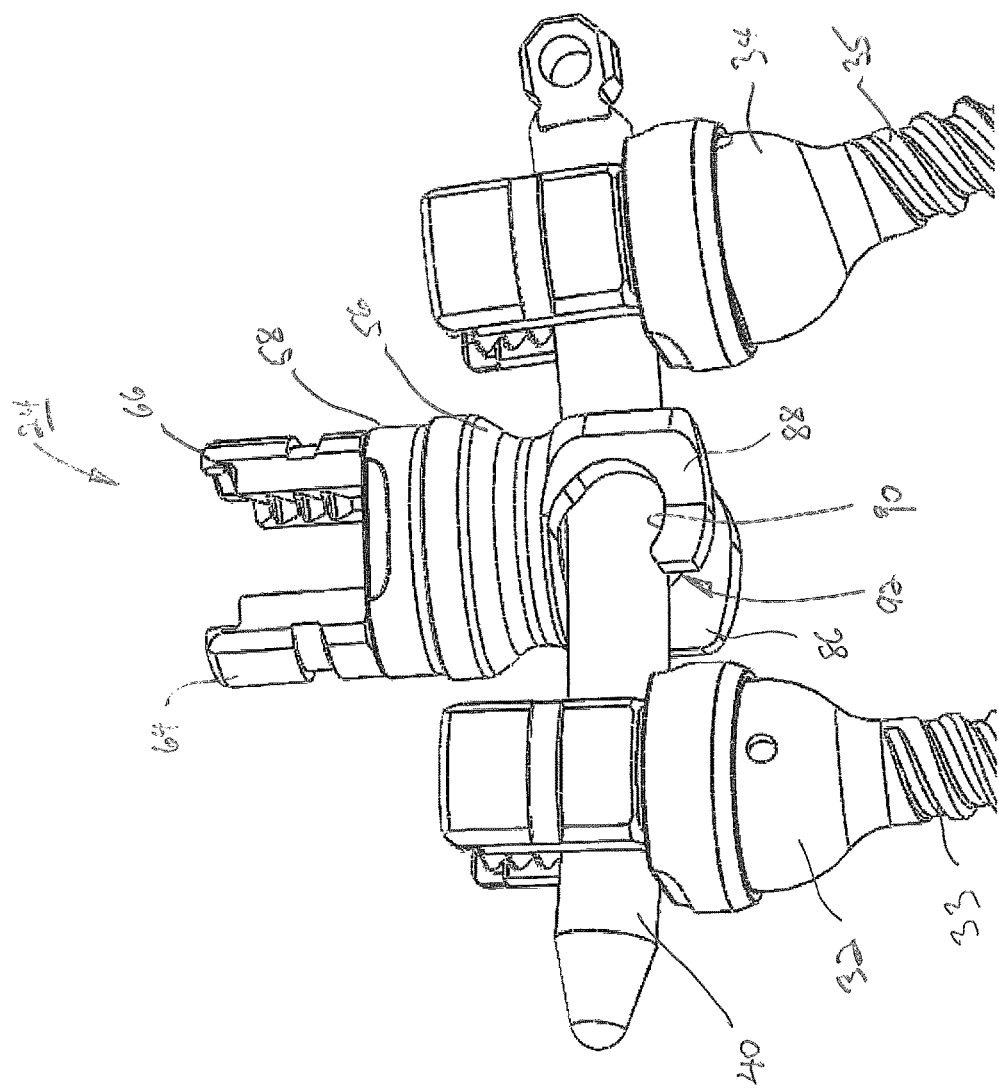

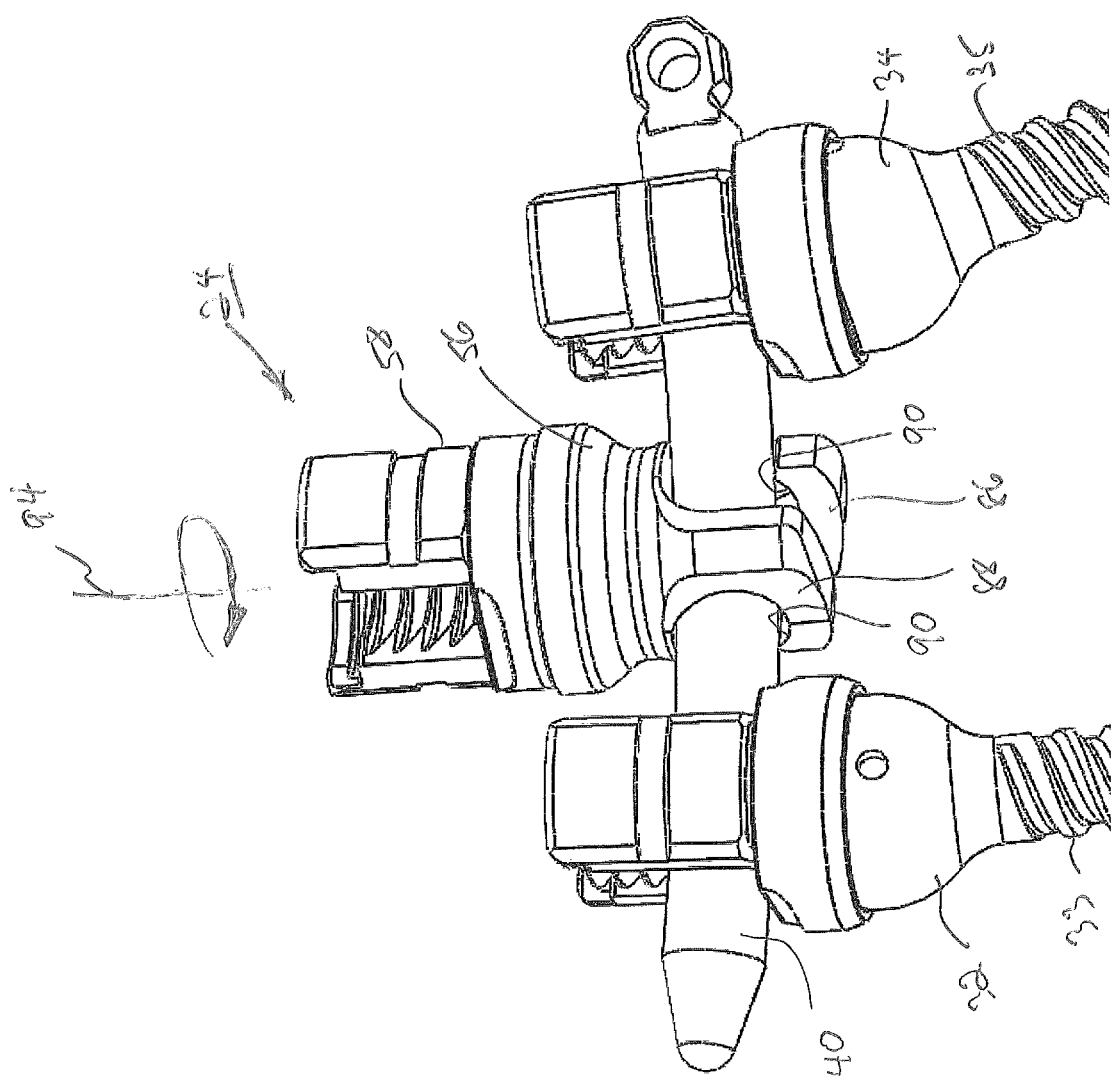

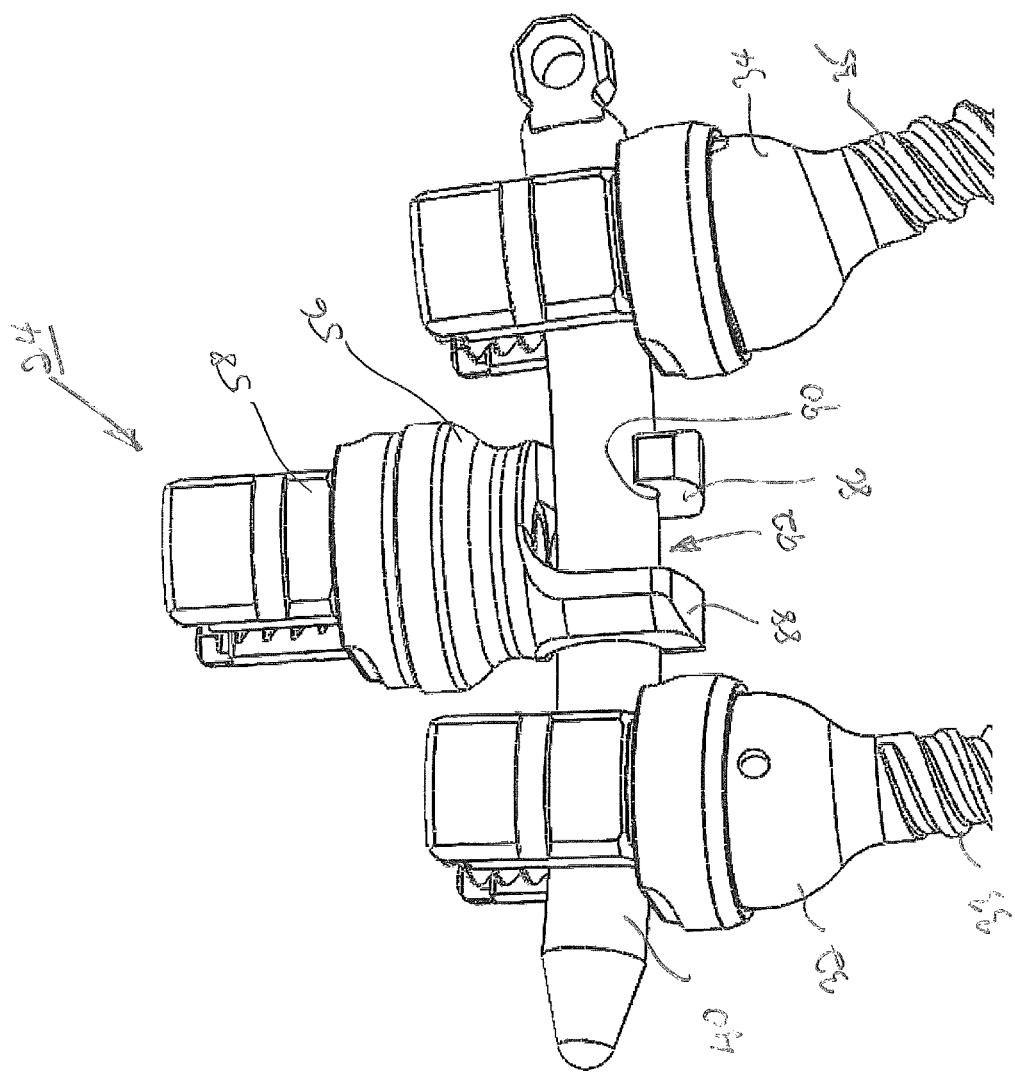

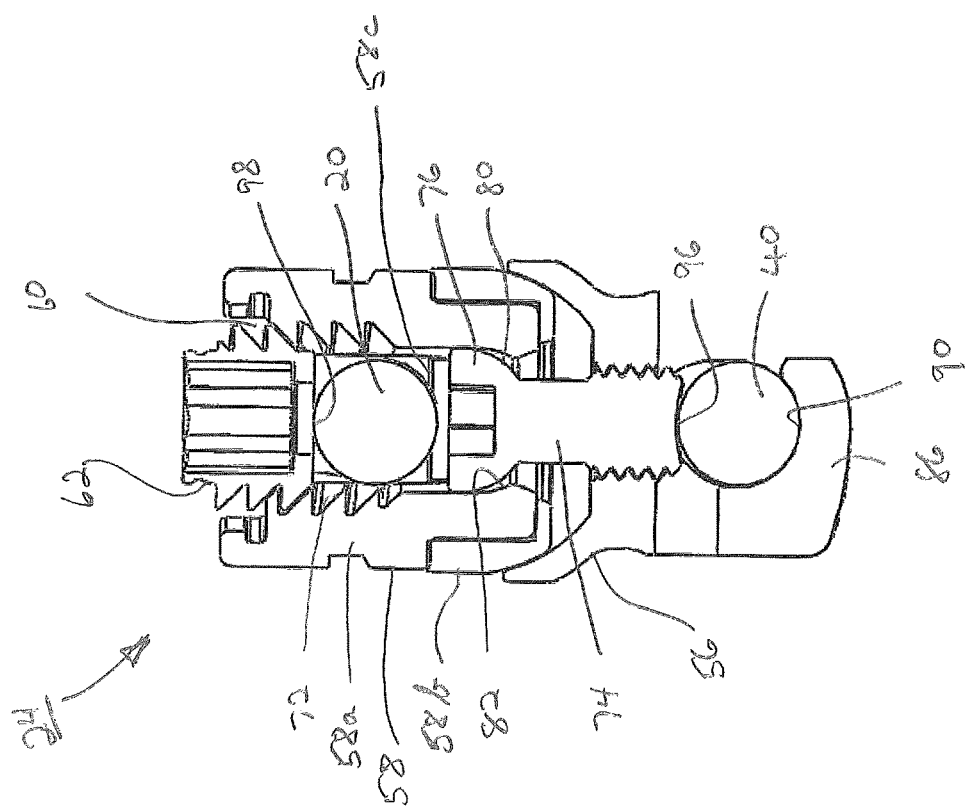

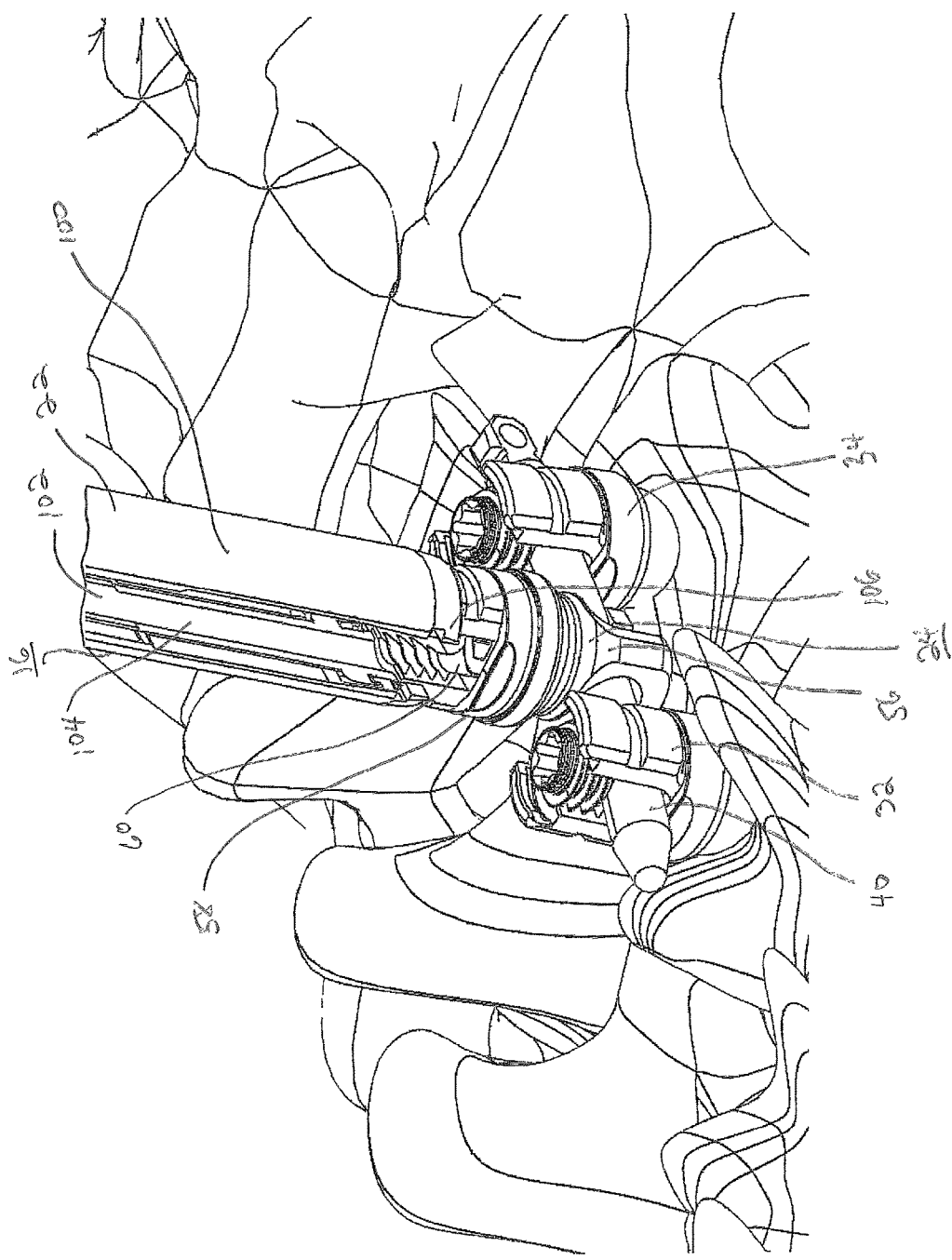

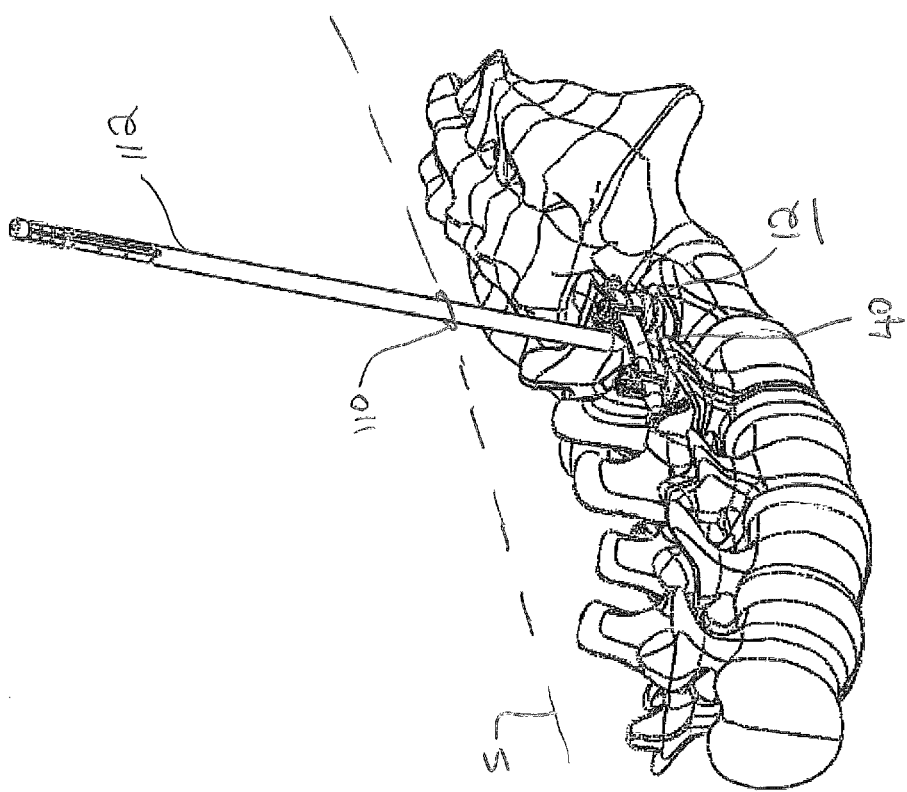

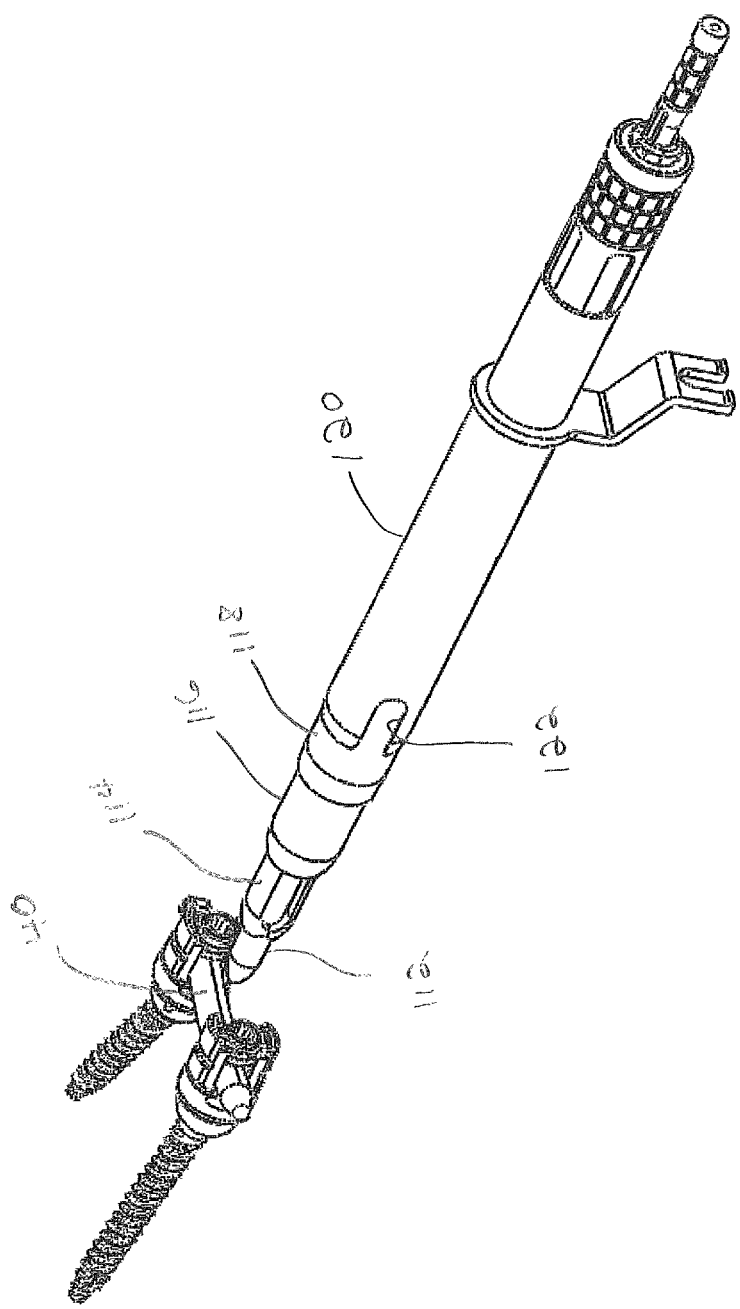

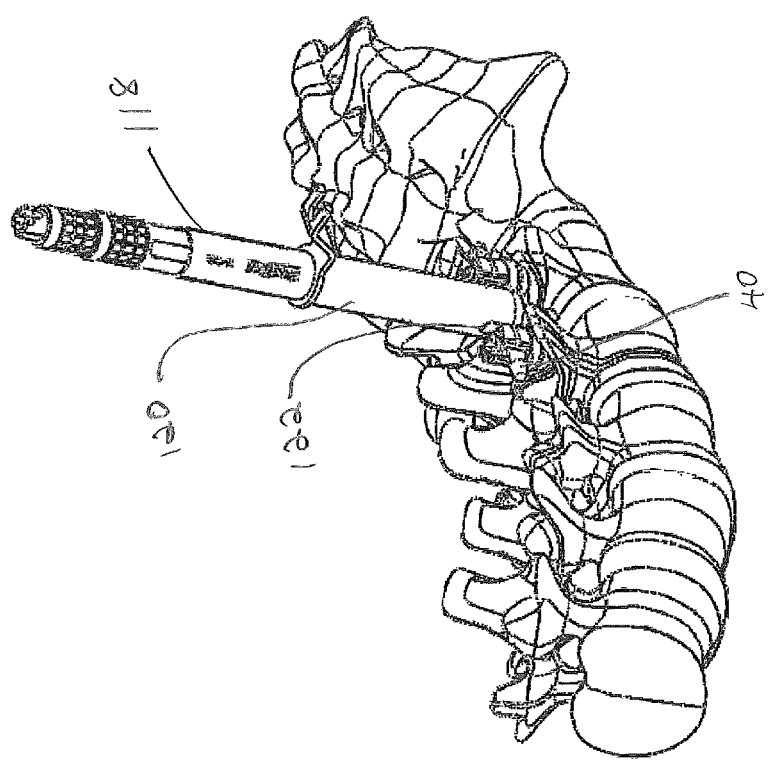

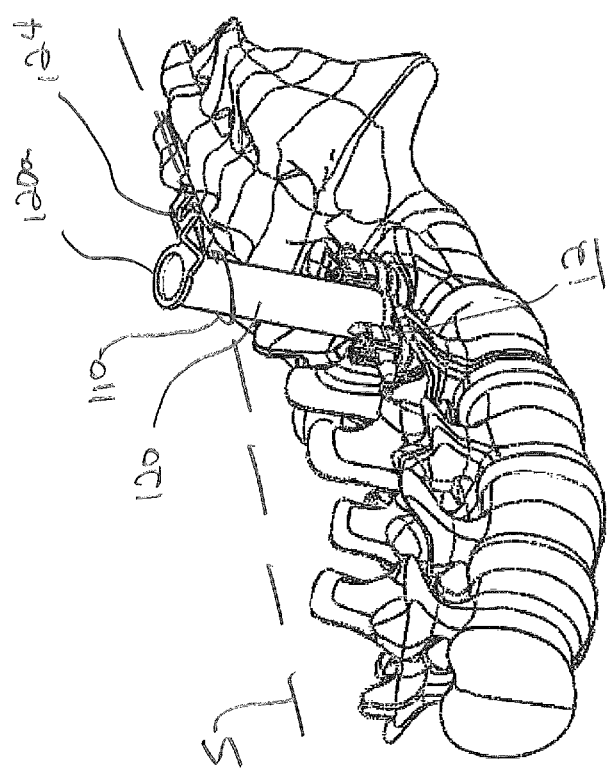

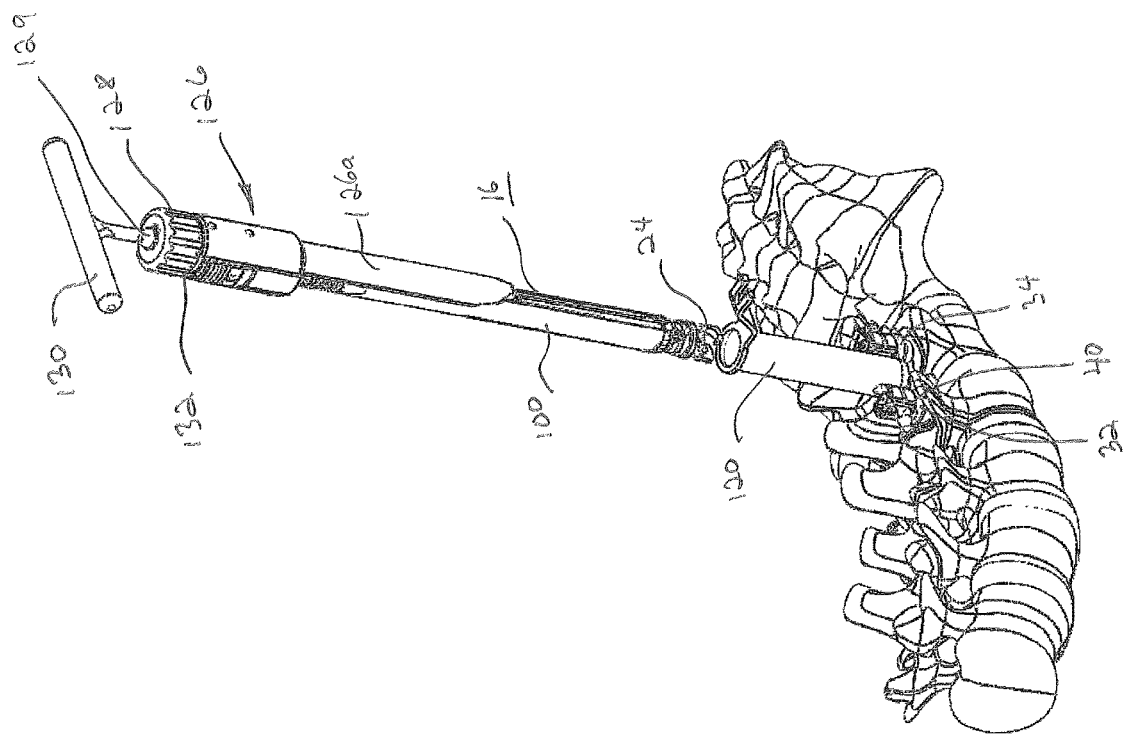

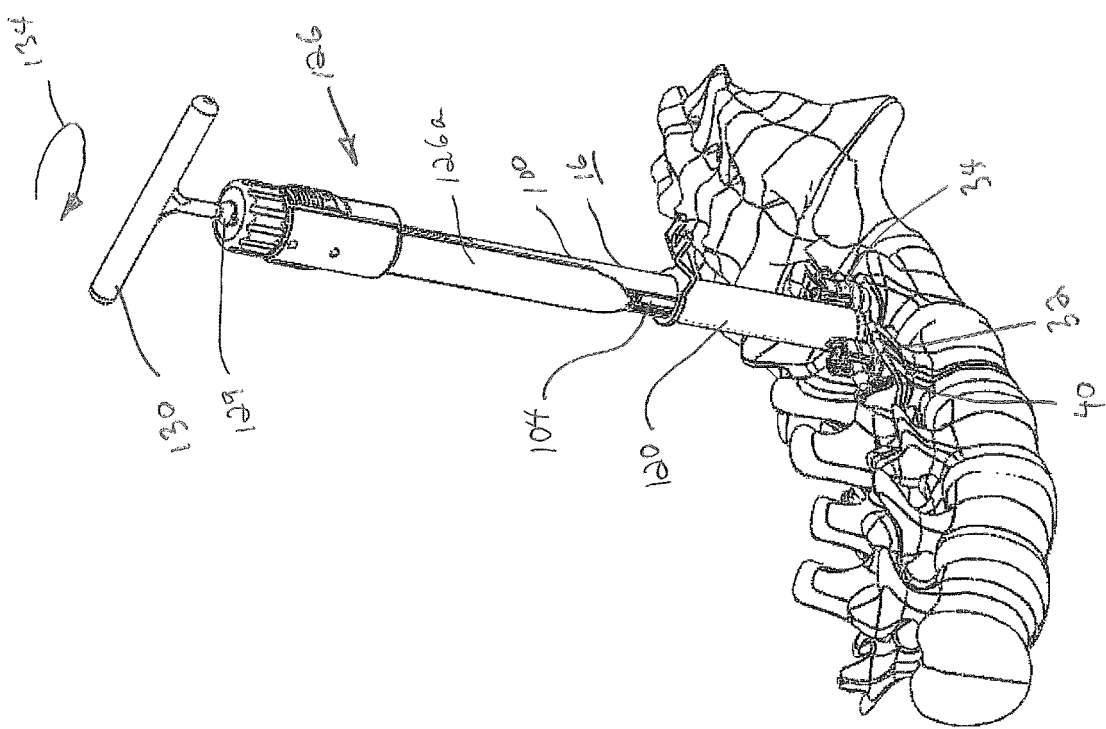

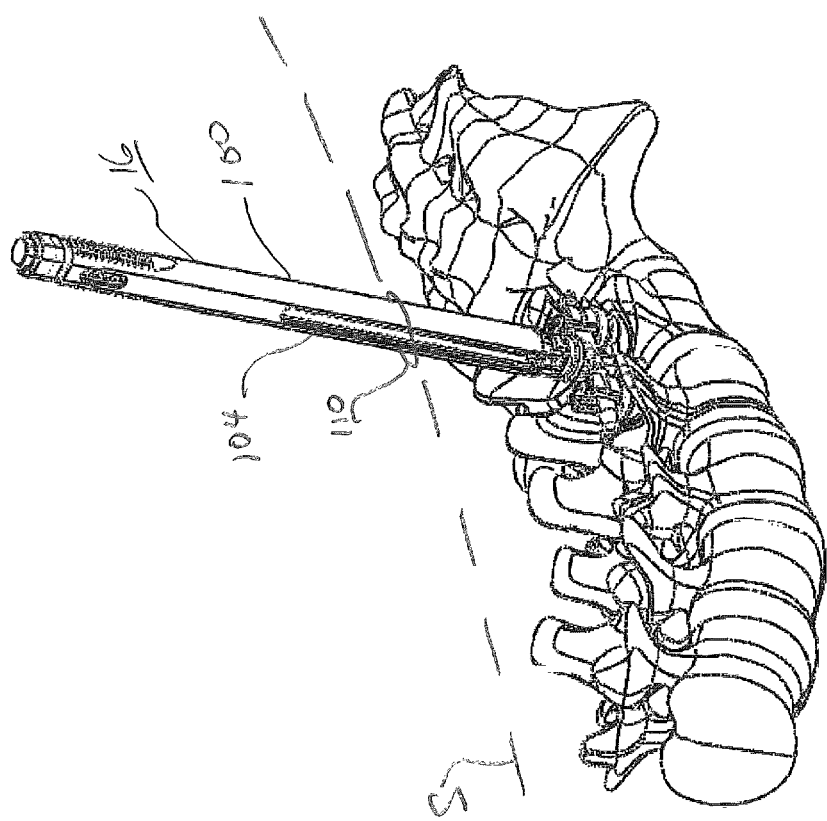

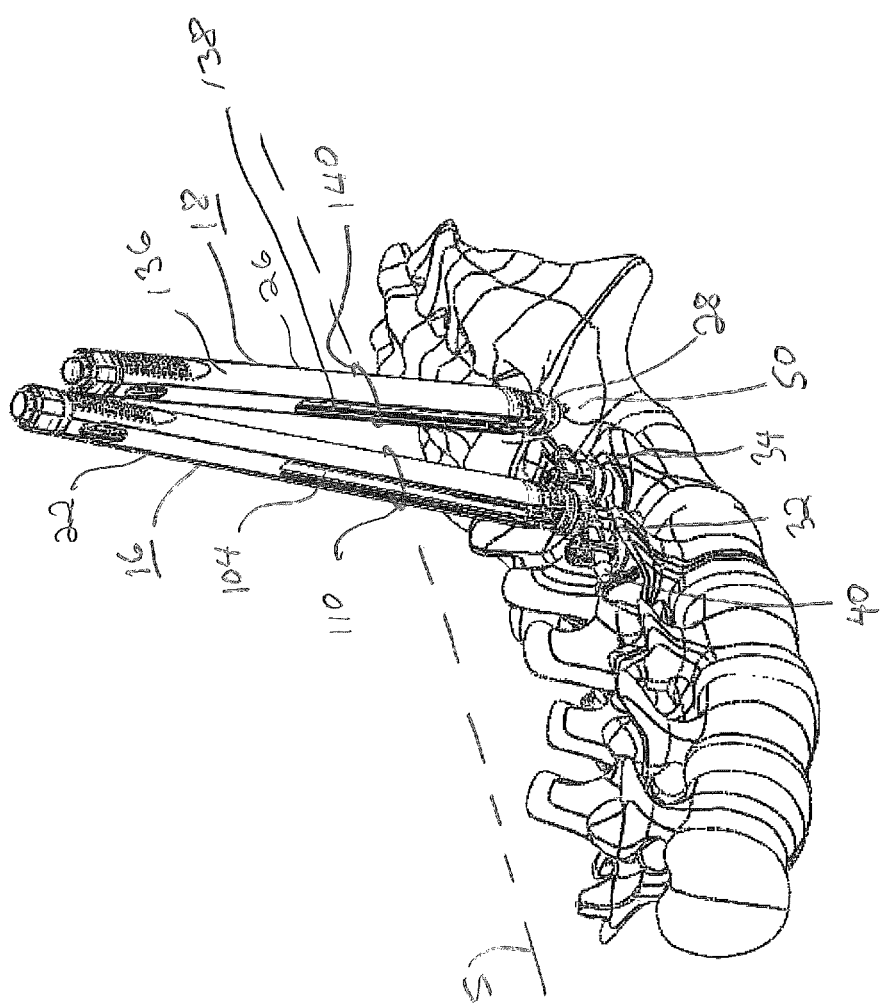

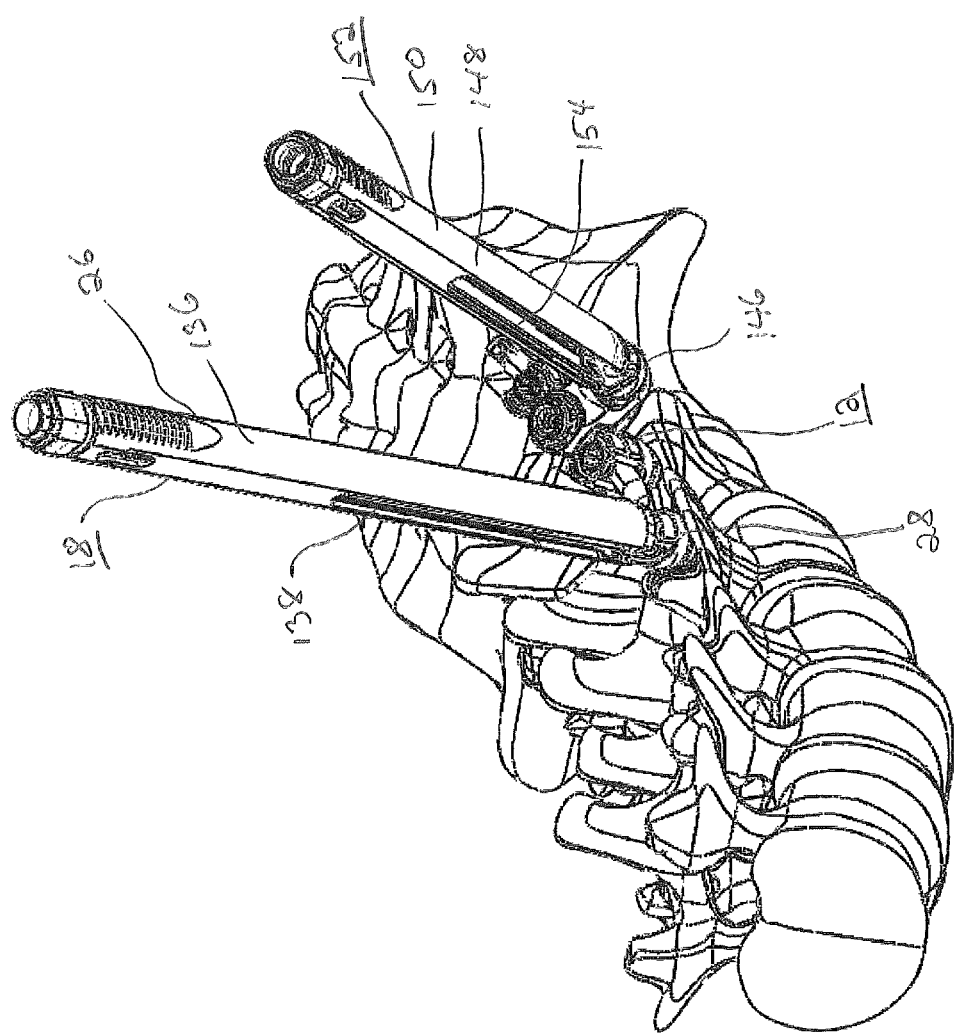

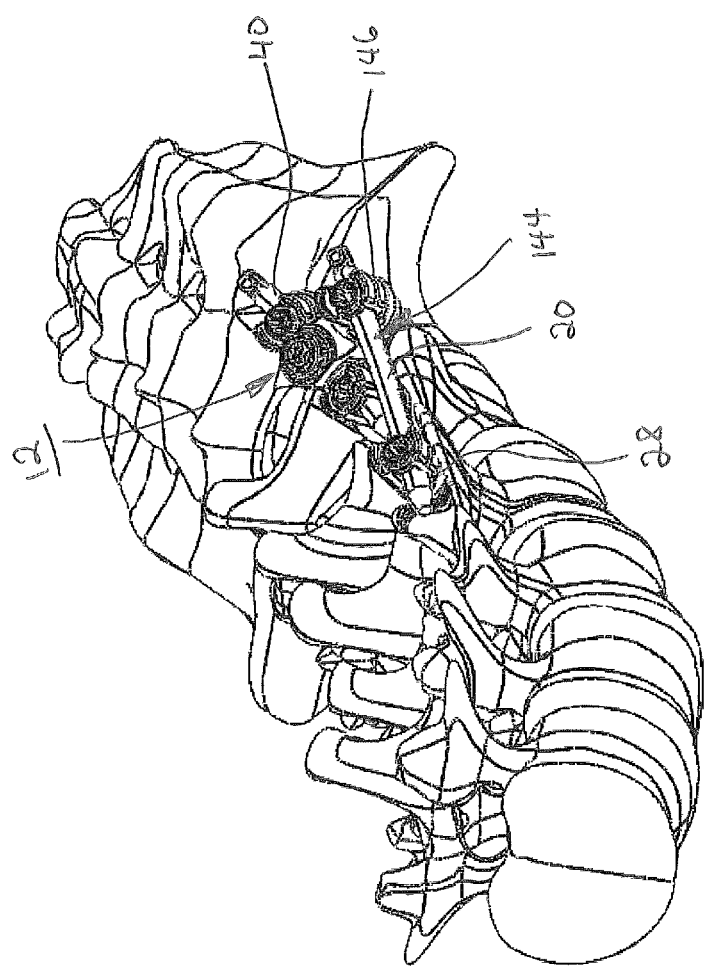

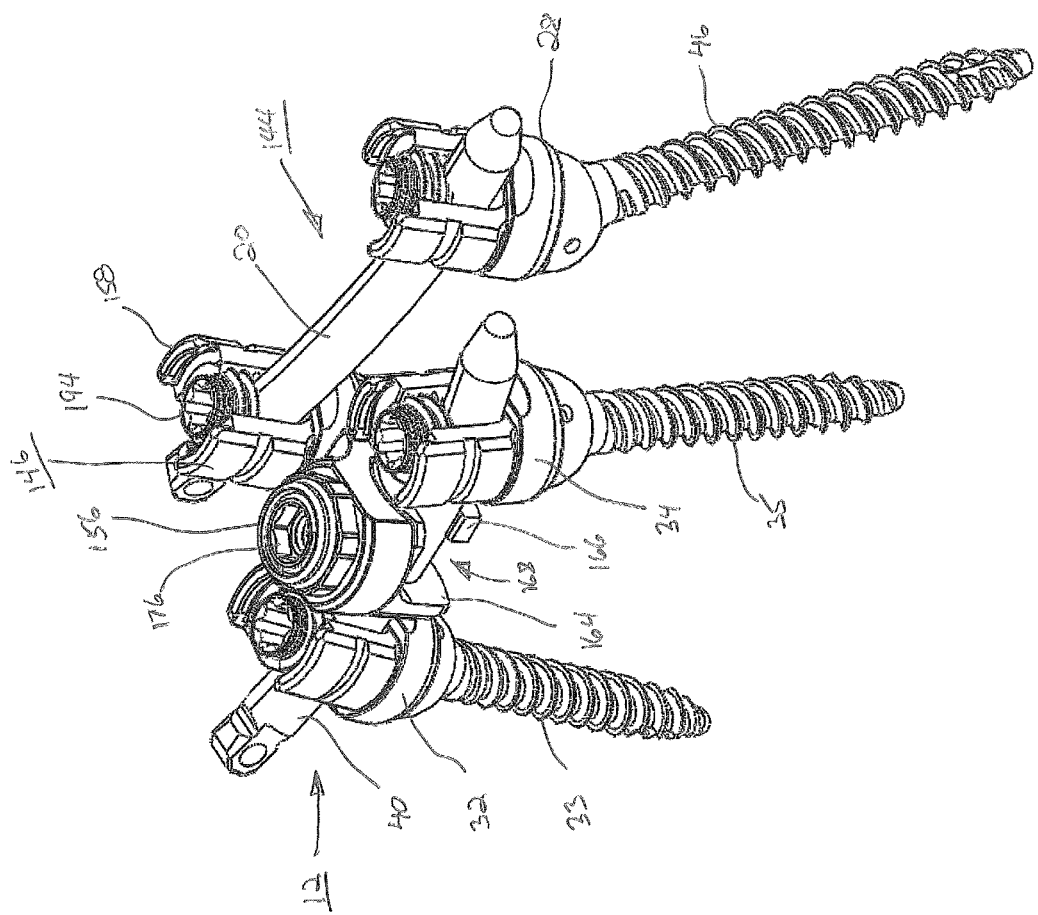

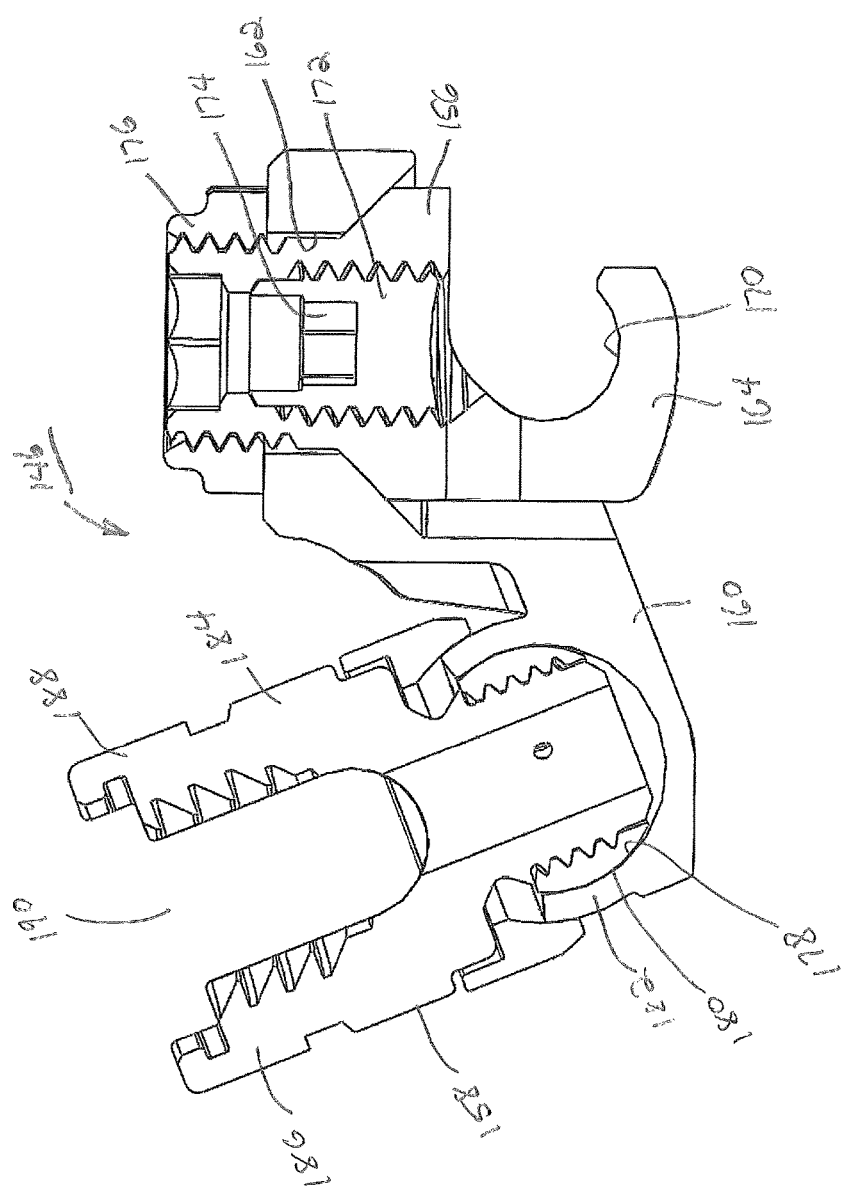

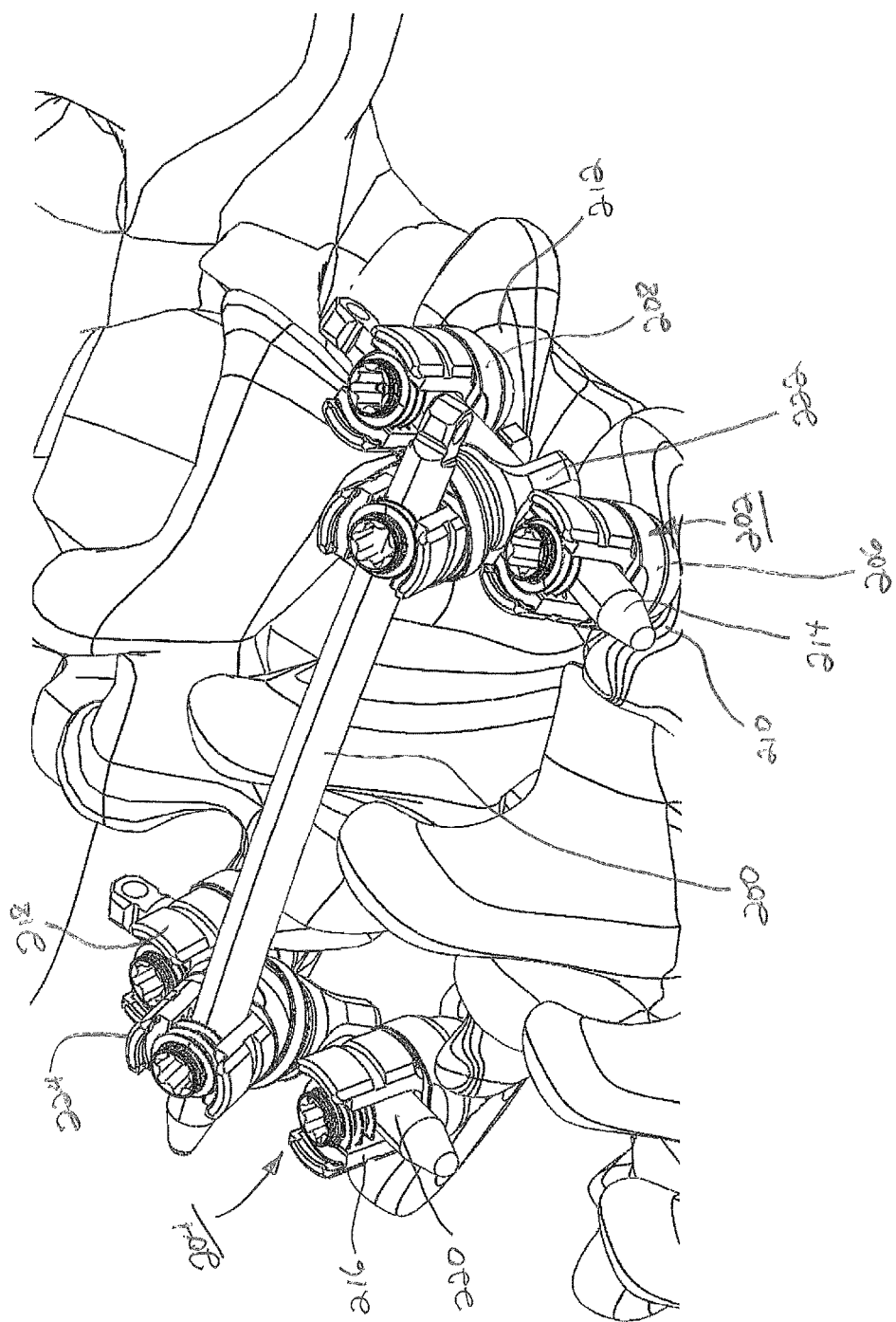

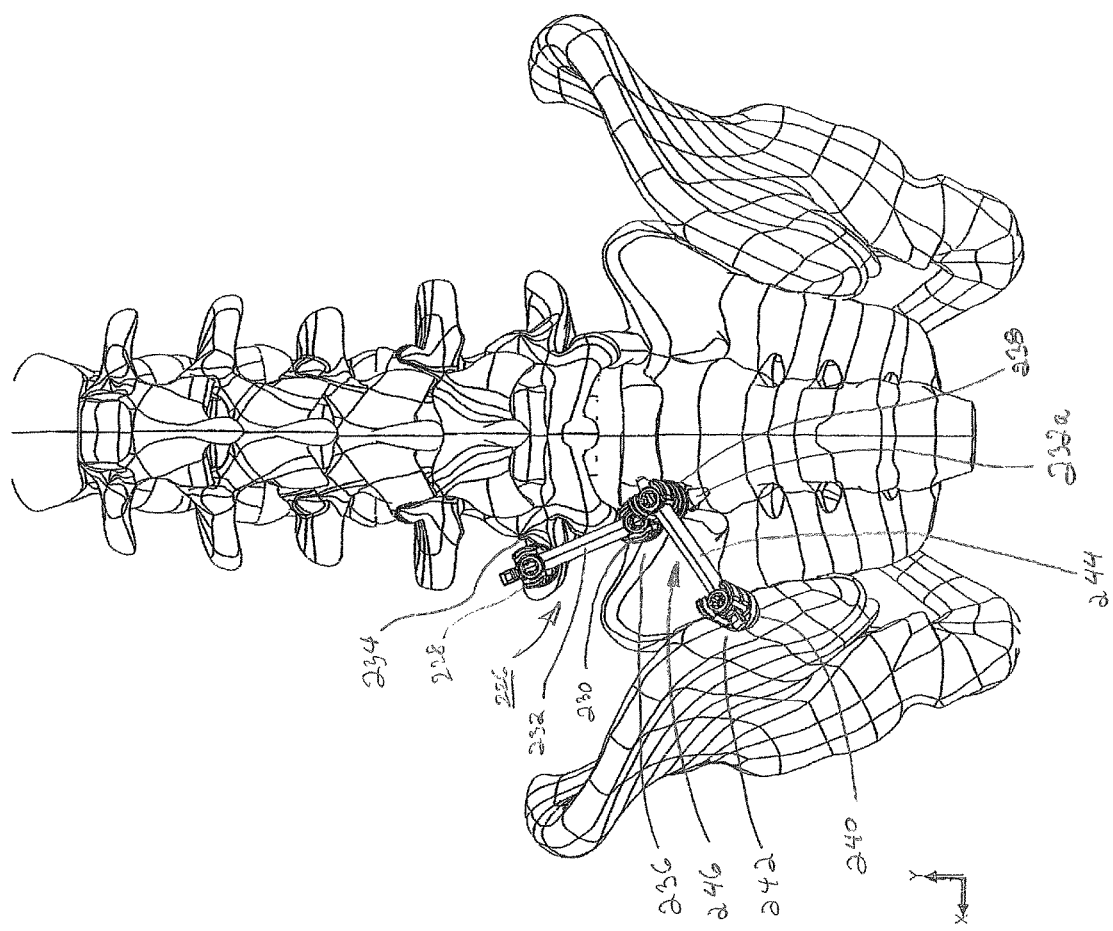

APPARATUS AND DEVICES FOR PERCUTANEOUSLY EXTENDING AN EXISTING SPINAL CONSTRUCT

CROSS-REFERENCES TO RELATED APPLICATIONS

This application is a continuation of U.S. application Ser. No. 14/186,550, filed Feb. 21, 2014, now U.S. Pat. No. 9,113,962, which is a continuation of U.S. application Ser. No. 13/470,390, filed May 14, 2012, now U.S. Pat. No. 8,657,826, which claims the benefit of U.S. Provisional Application No. 61/568,199, filed on Dec. 8, 2011, the entire contents of these applications being incorporated by reference herein.

BACKGROUND

The present disclosure contemplates devices and instrumentation for extending an existing spinal construct, and more particularly to procedures for achieving such extension minimally invasively, and preferably percutaneously.

An emerging trend in spinal fixation is an increased incidence of adjacent disc degeneration subsequent to a previous fixation or fusion. This subsequent degeneration often requires fixation or fusion of additional levels of the spine. It is common in current techniques to expose the entire prior construct to access all of the existing bone fasteners to permit removal of the connecting member spanning the fasteners. The connecting member is removed and replaced with a longer member, such as a rod, to engage an additional bone fastener added at the new levels to be instrumented.

This exposure of the prior fixation construct disrupts the existing construct complicating and lengthening the surgical procedure for adding the additional level of fixation. Such techniques are particularly problematic for a fixation construct spanning three or more vertebral levels. As such, there is a need for a device and method that facilitates the addition of further levels of fixation.

Several recent advancements have been disclosed that describe the extension of existing spinal constructs with minimal disruption to the existing construct. One example is shown in co-pending commonly assigned U.S. application Ser. No. 12/797,682, entitled "Devices and Methods for Adding an Additional Level of Fixation to an Existing Construct", filed on Jun. 10, 2010 and published as No. 2010/0318131. Other examples include U.S. Pat. No. 7,976,567, entitled "Orthopedic Revision Connector", issued on Jul. 12, 2011 to William B. Null, et al. and U.S. Pat. No. 8,021,399, entitled "Rod Extension for Extending Fusion Construct", issued on Sep. 20, 2011 to Stephen Ritland. While these approaches represent improvements in revision techniques and devices, it would be advantageous to not only extend an existing construct in a relatively non-disruptive manner to such construct, but to do so in a minimally invasively and, preferably percutaneous procedure.

SUMMARY

It is an object of the present invention to provide apparatus and devices for adding an additional construct to an existing spinal construct in a patient preferably minimally invasively and more preferably, percutaneously.

DESCRIPTION OF THE FIGURES

FIG. 1 is a perspective view of a portion of a patient's spine showing instrumentation disclosed herein to extend an existing ipsilateral spinal construct.

FIG. 2 is a perspective view of a portion of a patient's spine showing an existing spinal construct extended ipsilaterally by one level with an additional inline spinal construct in accordance with the apparatus of FIG. 1.

FIG. 4 is a side view of a rod connector in accordance with one arrangement of the disclosure in a position for attachment to an existing spinal rod of the existing spinal construct shown in FIG. 3.

FIG. 5 is an end cross-sectional view of the rod connector of FIG. 3 engaged to the existing spinal rod.

FIG. 6 is a further view of the rod connector of FIG. 4 showing the rod connector placed on the existing spinal rod.

FIG. 7 is a further view of the rod connector of FIG. 6 showing the rod connector partially rotated on the existing spinal rod so as to initiate engagement of the rod connector with the existing spinal rod.

FIG. 8 is a further view of the rod connector of FIG. 7 showing the rod connector fully rotated and in a final position in engagement with the existing spinal rod.

FIG. 9 is an end cross-sectional view similar to that of FIG. 5 showing the securement of the rod connector to the existing spinal rod and the securement of an additional spinal rod to the rod connector.

FIG. 10 is an enlarged perspective view of the rod connector extension assembly attached to the existing spinal rod of the existing spinal construct.

FIG. 11 is a perspective view of a patient's spine showing instrumentation for targeting the position of an existing spinal construct within a patient.

FIG. 12 is a perspective view of dilating instruments including an access port for use in a percutaneous procedure for extending an existing spinal construct.

FIG. 13 is a perspective view of the dilating instruments of FIG. 12 positioned on existing spinal construct in a patient's spine.

FIG. 14 is a further view of FIG. 13 with the dilating instruments removed and the access port positioned within the patient's spine adjacent the existing spinal construct.

FIG. 15 is a further view of FIG. 14 showing a rod connector extension assembly attached to an insertion tool in preparation for insertion through the access port.

FIG. 16 is a further view of FIG. 15 showing placement of the rod connector extension assembly into the access port and rotation thereof by the handle of the insertion tool.

FIG. 17 is a further view of FIG. 16 with the insertion tool removed and the rod connector extension assembly attached to the existing spinal rod within the patient's spine.

FIG. 18 is a further view of FIG. 17 showing the placement of a spinal implant extension assembly through the skin of the patient attaching an additional spinal implant to an additional vertebral body.

FIG. 19 is a perspective view of a portion of a patient's spine showing instrumentation disclosed herein to extend an existing ipsilateral spinal construct with an offset additional spinal construct.

FIG. 20 is a further view of FIG. 19 with the extensions removed and showing an existing spinal construct extended ipsilaterally by one level with an offset additional spinal construct.

FIG. 21 is an enlarged perspective view of the existing spinal construct and offset extension of FIG. 20.

FIG. 22 is an end cross-sectional view of the offset rod connector of FIG. 21.

FIG. 23 is a further view of FIG. 20 showing an access port positioned within the patient's spine adjacent an existing spinal construct, the port sized to receive an offset rod connector extension assembly.

FIG. 24 is a perspective view of an additional construct added as a cross connector to two existing contralateral spinal constructs using devices and instrumentation disclosed herein.

FIG. 25 is a posterior view of a portion of the patient's spine showing an additional construct extending an existing spinal construct to a further bony segment, such as the illium.

DESCRIPTION OF THE EMBODIMENTS

Figure 3:
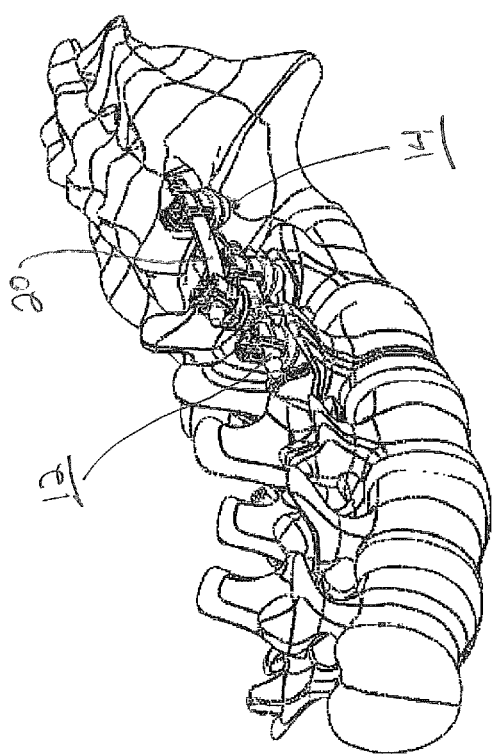
FIG. 3 is an enlarged perspective view of the existing spinal construct and inline extension of FIG. 1.
Figure 63:
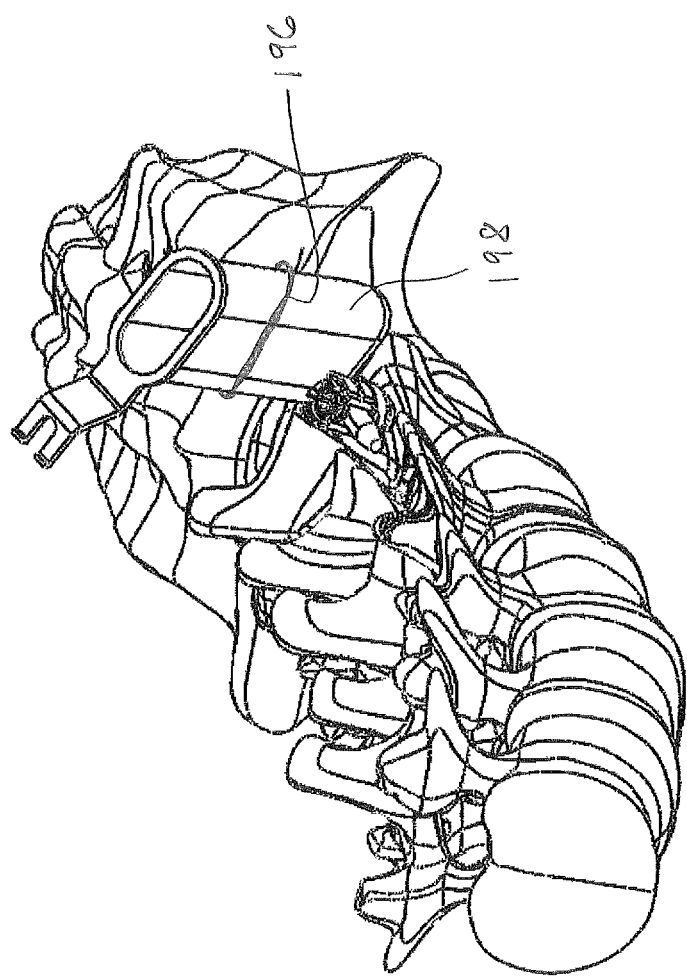

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Referring to FIGS. 1 and 2, an apparatus 10 is shown for extending an existing spinal construct 12 by adding an additional spinal construct 14 so as to increase the level of spinal fixation in a patient having previously undergone spinal fusion or other spinal surgery. The apparatus 10 generally comprises a rod connector extension assembly 16, a spinal implant extension assembly 18 and an additional spinal rod 20 serving as a connecting element interconnecting the existing spinal construct 12 and the additional spinal construct 14. As illustrated, the existing spinal construct 12 as well as the additional spinal construct 14 are located ipsilaterly in the spine in this particular arrangement. As will be described in more detail below, rod connector extension assembly 16 comprises an elongate extension 22 releasably attached to a rod connector 24. Spinal implant extension assembly 18 comprises an elongate extension 26 releasably attached to an additional spinal implant 28. Each of extension 22 and 26 is sized and of length to be accessible outside the patient's skin. The patient's skin or fascia is depicted as a phantom line S for illustrative purposes only, with the understanding that the level of the fascia relative to the fixation location on the spine will vary from patient to patient. Further shown is a rod introducer 30 that is used to introduce the additional spinal rod 20 into the spinal implant 28 and the rod connector 24 of the additional spinal construct 14 using a free hand technique. The details of rod introducer 30 are fully described in co-pending commonly assigned U.S. patent application Ser. No. 12/818,965 (the '965 Application), entitled "System for Percutaneously Fixing a Connecting Rod to a Spine", filed on Jun. 18, 2010, the disclosure of which is incorporated herein by reference in its entirety.

Referring now also to FIG. 3, further details of the additional spinal construct 14 and the existing spinal construct 12 are described. The existing spinal construct 12 comprises at least two previously implanted bone engaging implants 32 and 34 each of which is engaged respectively to a corresponding vertebra 36 and 38. Implants 32 and 34 are interconnected by an existing spinal rod 40 extending ipsilaterally therebetween. As shown, each of implants 32, 34 is a polyaxial pedicle screw having a lower threaded fastener portion 33, 35 (FIG. 4) for threaded engagement respectively in a pedicle of vertebra 36 and a pedicle of vertebra 38. Each implant 32, 34 includes a respective upper portion 42 and 44 defines a yoke each having a slot 43, 45 for receipt of the existing spinal rod 40 therein.

The additional spinal construct 14 comprises rod connector 24, additional spinal implant 28 and additional spinal rod 20. Spinal implant 28, as depicted in FIG. 3, is a polyaxial pedicle screw having a lower threaded portion 46 and an upper yoke portion 48 that articulates relative to threaded portion 46. The threaded portion 46 is threadedly engaged to a third spinal segment 50 as will be described. As depicted, spinal segment 50 is sacral segment S1 of the sacrum, it being understood that such spinal segment may be another vertebral body. The upper yoke portion 48 defines an open ended slot 52 for receipt and support therein of one end 20a of additional spinal rod 20 and is fastened to the yoke portion 48 by a set screw 54 or other suitable fastener. While additional spinal implant 28 is described as being a pedicle screw, it should be appreciated that depending upon the application additional spinal implant 28 may include other bone engaging implants with fasteners such as hooks, or rod connectors as will be described below with respect to alternative arrangements.

Rod connector 24 comprises a lower first portion 56 and an upper second portion 58 articulatingly attached to the first portion 56. The first portion 56 is attached to the existing spinal rod 40 as will be further described. The second portion 58 defines a yoke having an open ended slot 60 for receipt and support therein of the other end 20b of spinal rod 20 which is fastened to the second portion 58 by a set screw 62 or other suitable fastener. As illustrated in FIG. 3 the additional spinal construct 14 is considered to be inline with the existing spinal construct 12. In such an arrangement, the upper second portion 58 of the connector 24 is positioned above and generally in alignment with the axis of the existing spinal rod 40. The additional spinal rod 20 is positioned above bone engaging implant 34 with the axis of additional spinal rod 20 aligned generally parallel with the axis of the existing spinal rod 40. As such, the existing spinal rod 40 and the additional spinal rod 20 are spaced approximately the same distance from a mid-line plane through the spine of a patient. It should be appreciated that depending upon the anatomy the additional rod 20, while projecting above the existing rod 40, may not be parallel thereto.

Turning now to FIGS. 4 and 5, further the details of the rod connector 24 are described. The second portion 58 of the rod connector has a first section 58a and a second section 58b as shown in FIG. 5. First section 58a comprises a pair of opposed upstanding arms 64 and 66 that define a yoke having slot a 60. The lower end of the second section 58b is provided with a generally spherically shaped surface 68 for articulating movement on a similarly generally spherically shaped surface 70 formed on an interior surface of the first portion 56 as also seen in FIG. 5. Section 58a is attached to section 58b to constrain rotational movement but to allow slight axial movement therebetween. The articulating movement allows the first portion 56 and the second portion 58 to swivel and rotate with respect to each other between surfaces 68 and 70 when in an unlocked position. The upstanding arms 64 and 66 cooperatively define threads 72 for threaded receipt therein of set screw 62. A locking screw 74, retentively retained in the second portion 58, includes an upper head 76 and a lower portion 78. The lower exterior surface 80 of the head 76 is generally spherical to allow the articulating movement between the first and second portions 56, 58 as outer surface 80 engages spherically shaped interior surface 82. The head 76 is also provided with an interior socket 84 that is configured in a hex pattern or other suitable shape, such as a conventional Torx configuration, to engage a similarly configured feature on an inner shaft of an insertion tool for placement of the rod connector 24 on the existing spinal rod 40. The lower portion 78 of the locking screw 74 is threaded for threaded engagement with threads 85 extending through the upper end of the first portion 56 to permit engagement of the locking screw 74 with the existing spinal rod 40, as will be described.

With reference still to FIGS. 4 and 5, the lower end of the first portion 56 of rod connector 24 comprises a pair of spaced hooks 86 and 88 each of which includes a respective projecting rod engagement member 90. Hooks 86 and 88 are spaced from each other at a distance defining an opening 92 that allows the existing rod 40 to be received therebetween. In the position as shown in FIG. 5 the rod connector 24 is in an unlocked position whereby rod connector 24 may rotate about the axis of the existing spinal rod 40 and first portion 56 and second portion 58 of the rod connector 24 may relatively articulate.

With reference to FIGS. 6 through 8, the operation of the rod connector 24 during attachment to the existing spinal rod 40 is described. In FIG. 6 the rod connector 24 is shown as being placed between the existing implants 32 and 34 with the existing spinal rod 40 received in the opening 92 between hooks 86 and 88. In this position, the rod engagement members 90 are not in engagement with spinal rod 40 but straddle the existing rod 40. As shown in FIG. 7, the rod connector 24 is rotated about axis 94 to cause engagement between the rod engagement portions 90 and the existing spinal rod 40. Rotation of the rod connector 24 is effected by rotation of the insertion tool 126 (FIG. 15) that is engaged to the rod connector 24 in part by way of the locking screw 74. The insertion tool 126 applies pressure to section 58b of the second portion 58 which in turn applies pressure to first portion 56. This pressure draws first section 58a axially upward such that spherical surfaces 80 and 82 as well as spherical surfaces 68 and 70 are engaged. As such, when the insertion tool 126 is rotated the entire rod connector 24 is rotated. FIG. 8 shows completion of the rotation of the rod connector 24 with the engagement members 90 being in engagement with the existing spinal rod 40 and ready for secured attachment thereto.

Once the rod connector 24 has been rotated to the appropriate attachment position, the rod connector 24 is in position for receipt of the additional rod 20 and for securement to the existing spinal rod 40 as shown in FIG. 9. Before the additional rod 20 is received in the rod connector 24, the locking screw 74 is tightened by an inner shaft 129 supported within a housing 126a of the insertion tool 126, the inner shaft 129 terminating at its proximal end at handle 130 (FIG. 15). The inner shaft 129 and handle 130 rotate independently of housing 126a. The lower end 96 of the locking screw 74 engages the existing spinal rod 40 and thereby fixedly secures the first portion 56 of the rod connector 24 to the existing rod 40. In this stage, the second portion 58 of the rod connector 24 is still allowed a certain degree of angular movement and rotation with respect to the first portion 56 by interaction between spherical surfaces 80 and 82 as described above. This allows for irregularities of the spine and further manipulation of the second portion 58 of rod connector 24 for proper receipt of additional rod 20. Once the additional rod 20 placed in the slot 60 of rod connector 24, the set screw 62 is then inserted and threaded into the threads 72 of the rod connector 24. Tightening of set screw 62 by a suitable screwdriver causes the lower end 98 of the set screw 62 to engage the additional spinal rod 20 which in turn engages an upper interior surface 58c of second section 58b. This causes the second section 58b to engage first portion 56 thereby locking spherical surfaces 68 and 70 while pulling first section 58a upwardly against locking screw 74 thereby locking spherical surfaces 80 and 82. Thus, the first and second rod connector portions 56 and 58 are locked together and the existing spinal rod 40 and the additional spinal rod 20 are secured in a fixed locked position with respect to each other.

Turning now to FIG. 10, the details of the rod connector extension assembly 16 are described. The rod connector assembly 16 comprises elongate extension 22 that is releasably attached to the second portion 58 of the rod connector 24. Extension 22 comprises an elongate sleeve 100 that has a lumen 102 extending lengthwise through the sleeve 100 in communication with rod connector 24. The sleeve 100 includes a pair of opposed axially extending slots 104 that extend through the wall of sleeve 100 and communicate with the lumen 102. The slots 104 open through the distal end 106 of the sleeve 100 such that when the sleeve 100 is releasably attached to the rod connector 24 the slots 104 are aligned in communication with slot 60 in the second portion 58 of the rod connector 24.

Referring also to FIG. 1, the sleeve 100 of extension 22 has a proximal end 108 with a length of the sleeve being defined between the distal end 106 end the proximal end 108. The length is of such dimension such that when the rod connector 24 is placed through the skin S and approximates the position of the existing spinal rod 40, the proximal end 108 extends outside the patient whereby the proximal end 108 may be manipulated to attach the rod connector 24 to the existing spinal rod 40. The slots 104 extend axially toward the proximal end 108 for a portion of the length of the sleeve 100 such that the slots 104 also extend outside the patient when the distal end 106 of the sleeve 100 is secured to the rod connector 24. When the sleeve 100 is releasably secured to the second portion 58 of the rod connector 24 the sleeve 100 and the second portion 58 jointly move in common. As such, manipulation of the sleeve 100 allows for angular and rotational manipulation of the second portion 58, particularly in the stage after the first portion 56 has been fixedly secured to the existing spinal rod 40 by tightening of the locking screw 74 and prior to the placement of the additional spinal rod 20. Selective orientation of the slots 104 as well as positioning of the second portion 58 to a location best suited for receipt of the additional rod 20 can be achieved. The particular details of the extension 22 including the structure of the sleeve 100 and the method of releasably securing the sleeve 22 to the rod connector 24 are described fully in the '965 Application incorporated herein by reference in its entirety.

Having described the devices and instruments for extending an existing spinal rod construct in a patient, the procedures for such extension are now described with particular reference to FIGS. 11-18. The first procedure relates to percutaneously extending an existing spinal construct 12 as shown in FIG. 11 with an inline ipsilateral additional construct as described above. Using fluoroscopy or other suitable imaging techniques, the existing spinal rod 40 is initially targeted so as to establish the position of the existing rod 40 in the patient. A small first percutaneous incision 110 is made through the skin S of the patient, the incision 110 being approximately 10-20 mm in length, although other suitable dimensions may be used. A targeting rod 112 is placed through the incised puncture and pushed through the tissue of the patient down to the existing spinal rod 40. Once the access path has been created and the position of the existing rod 40 established a series of sequentially increasing dilating instruments are inserted over the targeting rod 112. As depicted in FIG. 12, the dilating instruments include an initial split dilator 114 that attaches temporarily to the existing rod 40, and dilating cannulas 116 and 118 of increasing diameter. The number of dilating cannulas may vary depending upon the procedure and the desired extent the incision 110 is to be expanded upon dilation. An access port 120 is then finally placed over the last dilating cannula 118, the access port 120 having a pair of opposed notches 122 that receive the rod 40 as shown in FIG. 13. The dilating instruments are then removed as illustrated in FIG. 14 leaving the access port 120 in place. The central longitudinal axis of the access port 120 is generally aligned with and perpendicular to the longitudinal axis of existing rod 40. A bracket 124 may be utilized to fix the access port 120 to the operating table so as to maintain the access port 120 in place throughout the surgical procedure. The proximal end 120a of the access port 120 projects out from the patient's skin S as shown in FIG. 14.

A rod connector extension assembly 16, including a rod connector 24 and an extension sleeve 100 as described above with respect to FIG. 10, is mated with an insertion tool 126, as shown in FIG. 15. The insertion tool 126 comprises outer housing 126a supporting inner shaft 129 that terminates at proximal end 128 of the tool 126 in rotatable handle 130. The distal end (not shown) of the inner shaft 129 has an engagement feature in engagement with the shaped socket 84 in the locking screw head 76. The insertion tool 126 includes a locking mechanism 132 for initially holding the first portion 56 and the second portion 58 of the rod connector 24 in a fixed rotational position while the inner shaft 129 and handle may freely rotate. The housing 126a, based on its configuration or other suitable reference marks, may be oriented to be aligned with the opening 92 between the hooks 86 and 88 of the rod connector 24 so that the opening 92 can be located with respect to the rod 40 by the positioning of the tool 126 during insertion of the rod connector extension assembly 16.

Rod connector extension assembly 16 is then introduced through the access port 120 by the manipulation of the extension sleeve 100 and insertion tool 126 from outside the patient until the rod 40 is received in the opening 92 between hooks 86 and 88 as shown in FIG. 6. The tool housing 126a is rotated clockwise as shown by arrow 134 in FIG. 16 approximately 90° to thereby rotate the rod connector 24 in a manner that causes engagement of the rod engagement members 90 with the existing spinal rod 40 and moving hooks 86, 88 to the position shown in FIG. 8. During rotation of the rod connector 24, the sleeve 100 is also rotated in common until the opposing slots 104 are aligned generally coaxially with the longitudinal axis of the existing spinal rod 40. As the distal end of the inner shaft 129 of the insertion tool 126 is engaged with the socket 84 of the locking screw 74, rotation of the handle 130 causes threaded rotation of the locking screw 74 to thereby tighten and lock the first rod connector portion 56 to the spinal rod 40 in the stage as shown in FIG. 9 as described above. The insertion tool 126 and the access port 120 are then removed leaving the rod connector extension assembly 16 in place with the rod connector 24 attached to the existing spinal rod 40 as shown in FIG. 17. As noted hereinabove, a certain degree of angulation and rotation of the rod connector second portion 58, as well as the extension sleeve 100 attached thereto in common movement therewith, is permitted with respect to the rod connector first portion 56. The rod connector 24 is thereby inserted through the access port 120 and attached to the existing rod 40 in a top loading procedure without disturbing the existing implants 32 and 34 or the previous connections to the existing rod 40. The top loading allows a surgeon to insert the rod connector 24 and connect it to the existing rod 40 from above the spine facilitating the percutaneous procedure.

Turning now to FIG. 18, the engagement of the additional spinal implant 28 as a component of the additional spinal rod construct 14 is described. Spinal implant extension assembly 18 comprises second elongate extension 26 which includes a second sleeve 136 releasably secured to the additional spinal implant 28. Spinal implant 28 is described as noted above with reference to FIG. 3 as being a polyaxial pedicle screw in this arrangement. Sleeve 136 has a pair of opposing slots 138 extending therethrough, the slots 138 being aligned and in communication with the slot 52 in the upper yoke portion 48 (see FIG. 3) of the spinal implant 28. The additional spinal implant 28 is percutaneously attached to the pedicle of sacral segment S1 of the sacrum 50 through a small second percutaneous incision 140 made through the skin S of the patient, separate and apart from the first incision 110. The incision 140 is approximately 10-20 mm in length. The dilation of incision 140 and the percutaneous attachment of spinal implant 28 to a spinal segment such as sacrum 50 is fully described in the '965 Application. Once spinal implant 28 is attached to the sacrum 50 the second sleeve 136 as well as slots 138 project out from the patient through dilated incision 140 with the slots 138 being rotatably manipulable upon rotation of sleeve 136 to be aligned with slots 104 of extension 22 as shown in FIG. 18.

With the rod connector 24 being attached to existing spinal rod 40 and with additional spinal implant 28 being attached to the third spinal segment such as sacrum 50, the additional spinal rod 20 is now ready to be implanted. Referring back now to FIG. 1 elongate extensions 22, 26 project outwardly from the patient's skin S with the slots 104 and 138 of the respective extensions 22 and 26 being oriented in substantial alignment with each other. As such, the slot 60 in the rod connector second portion 58 and the slot 52 in the yoke portion 48 of the spinal implant 28 are likewise in alignment. The additional spinal rod 20 is suitably attached adjacent end 20a to the rod introducer 30 in a manner that permits pivotal movement of the rod 20 relative to the introducer 30.

Rod 20 is then introduced in this procedure through incision 140 at an extreme cephalad or caudal location of the spinal implant extension assembly 18. Alternatively, the rod 20 may be introduced through incision 110 instead of incision 140. In the approach using incision 140, the rod 20 is oriented at a 45° angle relative to the shaft 142 of the rod introducer 30. The introducer 30 is manipulated by hand so that the leading end 20b of the rod 20 passes through slots 138 of the spinal implant extension assembly 18 and subsequently or simultaneously through incision 140. If necessary, the angle of the rod 20 may be adjusted to facilitate entry of the rod 20 through incision 140.

Once below the skin surface S the rod 20 can be advanced subcutaneously beneath the fascia toward the rod connector extension assembly 16. The sides of the slots 138 in extension sleeve 136 further act as guides to keep the rod 20 aligned during subcutaneous advancement until the rod 20 enters slots 104 of the rod connector extension assembly 16. Rod 20 may then be seated into slot 60 of rod connector 24 and slot 52 of spinal implant 28 by manipulation of the rod introducer 30 or by a suitable rod persuader (not shown). Once the rod 20 is fully seated in the rod connector 24 and the spinal implant 28, rod introducer may be disengaged from end 20a. Set screw 54 may then be inserted through extension 26 by a suitable driver to engage the threads of yoke 48 to secure end 20a to spinal implant 28. Similarly, set screw 62 may then be inserted through extension 22 by a suitable driver to engage the threads of second portion 58 of the rod connector 24 to secure end 20b to the rod connector 24. Extensions 22 and 26 may then be released respectively from rod connector 24 and spinal implant 28 and the incisions 110 and 140 suitably closed. As such, the inline ipsilateral extension of the existing spinal construct 12 by additional spinal construct 14 as shown in FIG. 3 is complete. Further details of the subcutaneous rod placement, rod persuasion and securement of the rod to the spinal implant 28 and rod connector 24 are described in the '965 Application.

In the procedure just described, additional rod 20 is introduced exteriorly of the extension assemblies through an incision in common with an extension assembly using only two incisions, namely incisions 110 and 140. In an alternative procedure, the rod 20 may be introduced into the surgical site through a third separate incision as fully described in the '965 Application. The free hand rod introducer 30 may be used to place rod 20 for implantation through the third separate incision. It should be appreciated, however, that non-free hand instruments that may be attached to one or both of the spinal implant extension assembly 18 and the rod connector extension assembly 16 where the third separate incision approach is desired. Such instruments, for example, are shown and described in U.S. Pat. No. 6,530,929, entitled "Instruments for Stabilization of Bony Structures", issued on Mar. 11, 2003 to Justis, et al., the disclosure of which is incorporated herein by reference in its entirety.

In another procedure a single incision may be used to provide the inline extension of an existing spinal construct. In this minimally invasive approach, a common incision may be formed joining the separate incisions 110 and 140 through which the rod connector extension assembly 16 and the spinal implant extension assembly 18 have been respectively introduced thereby forming a single incision. Alternatively, a single incision may be initially made through the skin S through which the rod connector extension assembly 16 and the spinal implant extension assembly 18 may be introduced. While such a single incision approach may not be regarded as percutaneous, it is considered a minimally invasive surgical approach. Once inserted through such a single incision whereby the rod connector 24 is attached to existing spinal rod 40 and additional spinal implant 28 is secured to a third vertebral body 50, the respectively attached extensions 22 and 26 project outwardly from the patient through the single incision. Slots 104 and 138 in the extensions may then be oriented in a manner such that the slots are aligned in a facing orientation. The additional rod 20 may be introduced by rod introducer 30 exteriorly of either one of the extensions 22 and 26 but through the single incision as described above using slots 104 and 138 as guides. Such approach is further fully described in the '965 Application Alternatively, with the single incision approach, additional rod 20 may be introduced through the single incision between the extensions 22 and 26. With the slots 104 and 138 and the extensions extending outside the patient and oriented to face each other, a suitable rod holder may be used to place opposite ends of rod 20 into slots 104 and 138 and move the rod 24 toward the patient and through the single incision until the respective ends of the rod 20 are seated respectively in rod connector 24 and spinal implant 28. Rod holding instruments and techniques for this approach, for example, are shown and described in U.S. Pat. No. 7,491, 218, entitled "Spinal Stabilization Systems and Methods Using Minimally Invasive Surgical Procedures", issued on Feb. 17, 2009 to Landry, et al., the disclosure of which is incorporated herein by reference in its entirety. In a variation using the single incision approach, the slots 104 and 138 may be formed each as a single slot through the wall of the extension sleeves 100 and 136 rather than as a pair of opposing slots, as described above. The length of such single slots 104 and 138 are likewise of extent to extend outside the patient when the respective extensions are in place in the patient. The single slots 104 and 138 are then arranged in facing orientation to receive the respective opposite ends of the rod 20 between the extensions 22 and 26 serving as guides for movement of the rod 20 through the single incision for seating in the rod connector 24 and the spinal implant 28.

While the existing spinal construct 12 has been described herein as being extended by a single level, it should be appreciated that the extension may comprise two or more levels with the devices and instruments set forth herein. In addition, while the devices and instruments described herein provide surgeons the ability to extend existing spinal constructs at least minimally invasively and more preferably, percutaneously, it should be understood that a surgeon may also use the described devices and instruments in an open procedure if that is the surgeon's surgical preference.

Having described the ipsilateral inline extension of an existing spinal construct hereinabove, devices and instruments for ipsilateral offset extension are now described with reference to FIGS. 19-23. The offset extension may be implanted in the same fashion as the inline extension, namely percutaneously, minimally invasively or, if the surgeon chooses in an open procedure.

As depicted in FIGS. 19-20, the existing spinal construct 12 is extended by an additional offset spinal construct 144 comprising an offset rod connector 146, additional spinal rod 20 and additional spinal implant 28. Additional spinal implant 28, as described above, is releasably attached to extension 26 including sleeve 136, implant 28 and extension 26 comprising the spinal implant extension assembly 18. Sleeve 136 has opposing slots 138 extending therethrough. Spinal implant extension assembly 18 is identical to that described above regarding the inline extension and the spinal implant 28 is implanted in the same manner.

Offset rod connector 146 is releasably attached to an elongate extension 148 comprising a sleeve 150. Offset rod connector 146 and extension 150 comprise an offset rod connector extension assembly 152. Sleeve 150 has opposing slots 154 extending therethrough. Extensions 26, 150 and their respective slots 138, 154 extend outwardly from the skin of the patient as described above when the extension assemblies 18, 152 are attached to the spine.

Turning now to FIGS. 21-22, the details of the offset rod connector 146 are described. Rod connector 146 comprises a first portion 156 and an offset second portion 158 supported by a support member 160. Second portion 158 is configured to be laterally offset from first portion 156 when the offset rod connector 146 is secured to existing spinal rod 40. First portion 156 is retentively supported by support member 160 within a throughhole 162 for rotational movement therewithin. First portion 156 comprises a pair of opposing spaced hooks 164 and 166 defining an opening 168 therebetween for receipt of existing spinal rod 40. Each hook 164, 166 has a projecting rod engagement member 170 for engagement with additional rod 20 as the first portion 156 is rotated relative to the support member 160 during insertion similar to rod connector 24 described above. A threaded interlocking screw 172 is threadably rotated within first portion 156, the locking screw 172 including an internal socket 174 for use in rotating and thereafter locking the first portion 156 to additional rod 20 by an insertion tool. An outer internally threaded nut 176 is provided to lock the first portion 156 to the support member 160.

Second portion 158 is retentively supported by the support member 160 for swivel movement through the interfacing of inner spherical surface 178 on support member 160 and the outer spherical surface 180 on an insert 182 threadably attached to a yoke 184. As such, second portion 158 also articulates relative to the first portion 156. Yoke 184 comprises a pair of opposing upstanding arms 186 and 188 defining a slot 190 therebetween for receipt of additional rod 20. The arms 186 and 188 include internal threads 192 for receiving a set screw 194 (FIG. 21) for securing additional rod 20 to the yoke 184 of second portion 158 upon tightening. Tightening of set screw 194 also locks the second portion 158 to support member 160 and thereby to the first portion 156. The structure and operation of the locking of additional rod 20 to yoke 184 and yoke 184 to the support member 160 are similar to that disclosed in co-pending commonly assigned U.S. application Ser. No. 11/560,587, entitled "Multi-axial Spinal Fixation System", filed on Nov. 16, 2006 and issued as U.S. Pat. No. 8,162,990, the disclosure of which is incorporated herein by reference in its entirety.

The procedure for attaching the offset rod connector 146 by manipulation of the offset rod connector extension assembly 152 to the existing spinal rod 40 is substantially the same as the attachment of the inline rod connector 24 by the rod connector extension assembly 16 as described above. An incision 196 is initially formed through the skin S, similar to incision 110, as shown in FIG. 23. The incision 196 is enlarged radially and laterally for insertion of an oval access port 198 similar to access port 120 but sized and configured to receive the offset rod connector assembly 152 therethrough for introduction of the offset rod connector 144 to the spine. The remainder of the procedure proceeds generally thereafter as described above.

In the completed offset additional spinal construct 144 as shown in FIGS. 21-22, the additional rod 20 is located laterally father away from the midline of the patient then the existing spinal rod 40. In an alternative arrangement, the offset rod connector 146 may be installed with the yoke 184 located interiorly of the existing spinal construct 12 such that the additional rod lies closer to the midline of the patient. The offset additional spinal construct 144 may also present a lower profile than the inline arrangement since the additional rod 20 does not lie above the existing construct illustrated in FIG. 1.

Turning now to FIG. 24, a further application of the devices and instruments of the subject disclosure is shown. Heretofore, the additional constructs have been added to existing spinal constructs ipsilaterally. In the application shown in FIG. 24, an additional spinal construct in the form of a cross connector 200 is added to a pair of existing contralateral spinal constructs 202 and 204 disposed on different sides of the spine each being offset from the spinal midline plane. Spinal constructs 202 and 204 are existing in the sense that they have been installed prior to the installation of the cross connector 200 even though the cross connector 200 may be placed during the same surgical procedure.

Existing spinal construct 202 is identical to existing spinal construct 12 described above and comprises at least two bone engaging implants 206 and 208 each of which is respectively engaged to a corresponding vertebra 210 and 212. Implants 206 and 208 are interconnected by a spinal rod 214 extending therebetween, implants 206 and 208 each being shown as a polyaxial pedicle screw. The other existing construct 204 is also identical to existing spinal construct 12 and comprises at least two bone engaging implants 216 and 218 each of which is respectively engaged to the same corresponding vertebrae 210 and 212, except on the opposite side of the midline of the spine. Implants 216 and 218 are also shown as being polyaxial pedicle screws which are interconnected by a spinal rod 220.

In a percutaneous procedure, the spinal constructs 202 and 204 are installed percutaneously in accordance with the devices, instruments and techniques described in the aforementioned '965 Application which has been incorporated herein by reference in its entirety. As such, implants 206 and 208 may each be implanted through a separate incision with interconnecting rod 210 being placed subcutaneously therebetween. Implants 216 and 218 may likewise be implanted percutaneously through separate incisions with interconnecting rod 220 similarly being placed subcutaneously therebetween.

In accordance with the subject technique, a spinal implant such as rod connector 222 may then be attached to an existing rod 214 and a spinal implant such as rod connector 224 may be attached to existing rod 220. Rod connectors 222 and 224 are each identical to the rod connector 24 described above with respect to the inline extension. Each of rod connectors 222, 224 is attached to respective rods 214 and 220 using a rod connector extension assembly identical to rod connector extension assembly 16, employing the same targeting, dilation and insertion procedures as described above with respect to the inline extension. Once the rod connector extension assemblies have been attached to the respective existing rods 214 and 220 and the respective extensions project outwardly from the patient, the additional spinal construct 200, such as a solid spinal rod, may be placed subcutaneously contralaterally between rod connectors 222 and 224 and secured thereto in accordance with the procedures of the '965 Application. In such a percutaneous procedure, three separate incisions may be formed on each side of the spine for a total of six small incisions. On each side of the spine two incisions may be used respectively for each of the pedicle screws and one incision for a rod connector 222 or 224. In a minimally invasive procedure, two common incisions may be formed on each side of the spine. Each common incision may be of such length so as to receive a pair of pedicle screws (206, 208 or 216, 218), an interconnecting rod such (214 or 220) as well as a rod connector (222 or 224) each of which is attached to a rod connector extension assembly. With an extension of each rod connector extension assembly projecting outwardly from the patient the cross connector rod 200 may then be placed subcutaneously beneath the skin between the contralateral common incisions to interconnect the rod connectors 222 and 224 in accordance with the procedures of the '965 Application. Thus, in the minimally invasive approach, a total of two common incisions may be formed on each side of the spine.

While the invention has been illustrated and described in detail in the drawings and foregoing description, the same should be considered as illustrative and not restrictive in character. For example, the existing spinal constructs described hereinabove are attached to the spinal segments such as adjacent vertebral bodies that may be extended with an additional spinal construct caudad to the sacrum or cephalad to one or more additional vertebral bodies. Variations are contemplated that include an additional construct that extends an existing spinal construct from spinal segments to other bony segments, which may be within the spine, such as vertebral bodies or the sacrum, or outside the spine, such as the Ilium. As shown in FIG. 25, an existing spinal construct 226 comprises a pair of bone engaging implants such as fasteners 228 and 230 and an existing spinal rod 232. Bone fastener 228 is a pedicle screw threadably secured to vertebral body 234, which as shown is lumbar segment L5. Bone fastener 230 is a pedicle screw threadably secured to the pedicle of the sacrum 236, which is shown as sacral segment S1. The existing rod 232 is inserted and attached to the bone fasteners 228 and 230 as described hereinabove. In this arrangement, rod 232 may have a length such that insertion end 232a has an extent projecting beyond bone fastener 230 toward the sacrum. While in the arrangements previously described an extent of the existing rod extending between bone fasteners is targeted for connection to a rod connector, in the arrangement of FIG. 25 the projecting rod end 232a is targeted. As such, a rod connector 238 similar to previously described rod connector 24 is attached to rod end 232a with a releasable rod connector extension assembly similar to rod connector extension assembly 16. Third bone engaging implant 240 such as an iliac screw similar to spinal implant 28 is threadably secured to the Ilium 242 with a releasable bone implant extension assembly similar to spinal implant extension assembly 16. Additional rod 244 similar to additional rod 20 is then attached to rod connector 238 and iliac screw 240 in a manner as described hereinabove to form the additional construct 246. As described, the procedure may be percutaneous, minimally invasive or an open procedure.

It is understood that only the preferred embodiments have been presented and that all changes, modifications and further applications that come within the spirit of the invention are desired to be protected.

What is claimed is:

1. A rod connector for attachment to a spinal rod in an existing spinal construct implanted in a patient, comprising:
   a first portion having an opening therethrough defining an axis, said first portion having a rod receiving opening to receive said existing spinal rod, said existing spinal rod having a longitudinal axis, said rod receiving opening having a first configuration capable of receiving said existing spinal rod in a direction transverse to said longitudinal axis and a second different configuration capable of locking the existing spinal rod to said first portion, said first portion including a rotatable rod engagement member configured to be spaced from said existing spinal rod in a first orientation and in engagement with an undersurface of said existing spinal rod upon rotation to a second orientation;
   a second portion having an opening, said axis of the opening of the first portion extending through said opening of said second portion, said rod engagement member being rotatable relative to said second portion; and
   a locking element supported by said second portion, said locking element having a first end accessible through said opening of said second portion and an opposite engagement end that upon movement of said locking element along said axis of the opening of the first portion extends into said rod receiving opening to thereby change said rod receiving opening from said first unlocked configuration to said second locked configuration, wherein said existing spinal rod is engaged between said engagement end of said locking element and said rod engagement member to thereby fixedly secure said first portion to said spinal existing rod.

2. The rod connector of claim 1, wherein said locking element is threaded and is threadably attached to threads fixed on said first portion.

3. The rod connector of claim 2, wherein said opening extends through said first portion and is interiorly threaded, and wherein said locking element is exteriorly threaded and is received in said interiorly threaded opening of said first portion.

4. The rod connector of claim 1, wherein said first portion includes a pair of spaced rotatable rod engagement members that includes said rotatable rod engagement member, said pair of rotatable rod engagement members being disposed for engagement with said existing spinal rod, each of said rod engagement members extending transversely relative to said axis of the opening of the first portion with distal free ends of respective rod engagement members projecting across said axis of the opening of the first portion in overlapping relation.

5. The rod connector of claim 4, wherein a rod engagement member of said pair of rod engagement members extends on either side of said axis of the opening of the first portion.

6. The rod connector of claim 1, wherein said second portion is rotatable relative to said first portion about said axis of the opening of the first portion.

7. The rod connector of claim 6, wherein said locking element is received in the opening of said first portion and the opening of said second portion.

8. The rod connector of claim 6, wherein said second portion articulates with respect to said first portion.

9. A rod connector for attachment to a spinal rod in an existing spinal construct implanted in a patient, comprising:
   a first portion having a first opening extending therethrough defining an axis, said first portion having a rod receiving opening configured to receive said existing spinal rod, said first opening being in communication with said rod receiving opening, said first portion being configured to attach to said existing spinal rod and comprising a pair of spaced hooks each including a projecting rod engagement member that are configured to engage said existing spinal rod upon rotation of said engagement members about said axis relative to said existing spinal rod;
   a second portion attached to said first portion, said second portion having a second opening in communication with said first opening, said second portion having an additional rod receiving opening configured for supporting an additional spinal rod, said additional rod receiving opening being in communication with said second opening;
   a locking member supported for movement in said first opening, said locking member comprising a first end having a surface for engagement with said existing spinal rod and a second opposite end accessible through said second opening, said locking member being movable axially within said first opening to cause said surface at said first end of said locking member to engage said existing spinal rod and lock said first portion to said existing spinal rod; and
   a fastening element movably supported by said second portion at a location for engaging said additional rod, said fastening element comprising an end configured upon movement relative to said second portion to engage said additional rod and thereby cause said additional rod to be secured to said second portion separately from said locking member locking said first portion to said existing spinal rod.

10. The rod connector of claim 9, wherein said second opening is disposed in substantial alignment with said first opening, said second portion being configured to support said additional spinal rod above and generally parallel to said existing spinal rod, said fastening element being disposed in said second opening.

11. The rod connector of claim 10, wherein said second portion of said rod connector comprises a pair of opposed upstanding arms defining a slot therethrough for receipt of said additional spinal rod.

12. The rod connector of claim 11, wherein said slot is in communication with said second opening, and wherein said fastening element is supported by said upstanding arms of said second portion to lock said first portion and said second portion in a locked position.

13. The rod connector of claim 12, wherein said upstanding arms define interior threads in communication with said slot and wherein said fastening element is a set screw comprising external threads in engagement with said interior threads on said upstanding arms.

14. A rod connector for attachment to a spinal rod in an existing spinal construct implanted in a patient, comprising:
a first portion configured to attach to said existing spinal rod upon rotation of a pair of spaced hooks extending from said first portion and defining therebetween a rod receiving opening for receiving said existing spinal rod in a non-secured position, said hooks each including a projecting rod engagement member projecting in opposite directions toward each other that are configured to engage said existing spinal rod upon rotation of said first portion relative to said existing spinal rod, said first portion having a first opening therethrough communicating with said rod receiving opening, said first opening defining an axis extending between said spaced hooks and about which said first portion is rotatable, said rod engagement members extending transversely relative to said axis with distal free ends of respective rod engagement members projecting across said axis in overlapping relation;
a second portion having a second opening therethrough in communication with the first opening of said first portion, said second opening providing access for fixedly securing said first portion to said spinal existing rod.

15. The rod connector of claim 14, wherein said second portion is configured for supporting an additional spinal rod.

16. The rod connector of claim 14, further comprising a fastening element supported by said second portion within said second opening to lock said first portion and said second portion in a locked position.

17. The rod connector of claim 14, further comprising a locking member movably supported within said first opening for fixedly securing said first portion to said existing spinal rod.

18. The rod connector of claim 14, wherein said second portion is rotatable relative to said first portion.

19. The rod connector of claim 18, wherein said first portion and said second portion each comprise spherically shaped surfaces in cooperating contact with each other for articulating relative movement of said first portion and said second portion.

* * * * *